(12) United States Patent
Colas et al.

(10) Patent No.: US 8,106,157 B2
(45) Date of Patent: Jan. 31, 2012

(54) POLYPEPTIDES HAVING MODULATORY EFFECTS ON CELLS

(75) Inventors: Pierre Colas, Santec (FR); Benoit de Chassey, Lyons (FR); Ivan Jacques Mikaelian, Lyons (FR); Brian B. Rudkin, Lyons (FR)

(73) Assignees: Ecole Normale Superieure de Lyon, Lyons (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/312,844

(22) PCT Filed: Nov. 30, 2007

(86) PCT No.: PCT/EP2007/010422
§ 371 (c)(1),
(2), (4) Date: Apr. 8, 2010

(87) PCT Pub. No.: WO2008/064907
PCT Pub. Date: Jun. 5, 2008

(65) Prior Publication Data
US 2011/0071087 A1    Mar. 24, 2011

(30) Foreign Application Priority Data
Dec. 1, 2006 (EP) .................................... 06291854

(51) Int. Cl.
C07K 1/00 (2006.01)
(52) U.S. Cl. ........................................................ 530/350
(58) Field of Classification Search .................. 530/350
See application file for complete search history.

(56) References Cited

U.S. PATENT DOCUMENTS
6,004,746 A  12/1999  Brent et al.

OTHER PUBLICATIONS

Colas P. "Combinatorial protein reagents to manipulate protein function" Current Opinion in Chemical Biology, 2000, 4:54-59.
Baines I. C. and Colas P. "Peptide aptamers as guides for small-molecule drug discovery" Drug Discovery Today, Apr. 2006, 11(7/8):334-341.
Colas P., et al. "Genetic selection of peptide aptamers that recognize and inhibit cyclin-dependent kinase 2" Nature, Apr. 1996, 380:548-550.
Colas P., et al. "Genetic Selection of Peptide Aptamers That Recognize and Inhibit Cyclin-Dependent Kinase 2* Identification of D-Peptide Ligands Through Mirror-Image Phage Display" Chemtracts Organic Chemistry, Jun. 1997, 10:527-532.
Bicicle M.B.T., et al. "Selection and characterization of large collections of peptide aptamers through optimized yeast two-hybrid procedures" Nature Protocols, 2006, 1(3):1066-1091.
Takayanagi H. "The Role of NFAT in Osteoclast Formation" Annals of the New York Academy of Sciences, Nov. 2007, 1116:227-237.
International Search Report issued by the International Searching Authority (ISA/EP) on May 2, 2008 in connection with International Application No. PCT/EP2007/010422.
Cohen B A, et al. "An artificial cell-cycle inhibitor isolated from a combinatorial library" Proc. Natl. Acad. Sci. USA, Nov. 1998, vol. 95, pp. 14272-14277.
Aramburu J, et al. "Calcineurin: a central controller of signaling in eukaryotes" EMBO reports, Apr. 2004, vol. 5, No. 4, pp. 343-348.
Yang Q, et al. "Cloning and identification of *NS5ATP2* gene and its spliced variant transactivated by hepatitis C virus non-structural protein 5A" World Journal of Gastroenterology. Jun. 2004, vol. 10, No. 12, pp. 1735-1739.
De Chassey B, et al. "An Antiproliferative Genetic Screening Identifies a Peptide Aptamer That Targets Calcineurin and Up-regulates Its Activity" Molecular & Cellular Proteomics, Mar. 2007, vol. 6, No. 3, pp. 451-459.
Stern P H. "The Calcineurin-NFAT Pathway and Bone: Intriguing New Findings" Molecular Interventions, Aug. 2006, vol. 6, No. 4, pp. 193-196.
Written Opinion of the International Searching Authority issued by the International Searching Authority (ISA/EP) on May 2, 2008 in connection with International Application No. PCT/EP2007/010422.

*Primary Examiner* — Maryam Monshipouri
(74) *Attorney, Agent, or Firm* — John P. White; Cooper & Dunham LLP

(57) ABSTRACT

The present invention relates to peptides and polypeptides having the sequence SAVTFAVCAL or variants thereof, capable of binding to Calcineurin and/or to NS5A-TP2 and to their use in therapy, as well as to nucleic acid sequences and vectors encoding these peptides and polypeptides, and to cells comprising said polypeptides, nucleic acid sequences or vectors. The invention further relates to the use of the peptides, polypeptides or their derivatives to bring about phenotypic changes in mammalian cells, particularly to up-regulate calcineurin activity. The invention finally relates to a method for intracellular identification of substances which bind to calcineurin and which modulate the physiological effects of calcineurin.

18 Claims, 17 Drawing Sheets

Figure 5

A) <u>Protein phosphatase 3 (formerly 2B), catalytic subunit, alpha isoform (calcineurin A alpha) [Homo sapiens] (accession number NP_000935)</u>

```
  1   msepkaidpk  lsttdrvvka  vpfppshrlt  akevfdndgk  prvdilkahl  mkegrleesv
 61   alriitegas  ilrqeknlld  idapvtvcgd  ihgqffdlmk  lfevggspan  trylflgdyv
121   drgyfsiecv  lylwalkily  pktlfllrgn  hecrhlteyf  tfkqeckiky  servydacmd
181   afdclplaal  mnqqflcvhg  glspeintld  dirkldrfke  ppaygpmcdi  lwsdpledfg
241   nektqehfth  ntvrgcsyfy  sypavceflq  hnnllsilra  heaqdagyrm  yrksqttgfp
301   slitifsapn  yldvynnkaa  vlkyennvmn  irqfncsphp  ywlpnfmdvf  twslpfvgek
361   vtemlvnvln  icsddelgse  edgfdgataa  arkevirnki  raigkmarvf  svlreesesv
421   ltlkgltptg  mlpsgvlsgg  kqtlqsatve  aieadeaikg  fspqhkitsf  eeakgldrin
481   ermpprrdam  psdanlnsin  kaltsetngt  dsngsnssni  q
```

B) <u>Protein phosphatase 3 (formerly 2B), catalytic subunit, beta isoform (calcineurin A beta) [Homo sapiens] (accession number NP_066955)</u>

```
  1   maapeparaa  pppppppppp  pgadrvvkav  pfppthrlts  eevfdldgip  rvdvlknhlv
 61   kegrvdeeia  lriinegaai  lrrektmiev  eapitvcgdi  hgqffdlmkl  fevggspant
121   rylflgdyvd  rgyfsiecvl  ylwvlkilyp  stlfllrgnh  ecrhlteyft  fkqeckikys
181   ervyeacmea  fdslplaall  nqqflcvhgg  lspeihtldd  irrldrfkep  pafgpmcdll
241   wsdpsedfgn  eksqehfshn  tvrgcsyfyn  ypavceflqn  nnllsiirah  eaqdagyrmy
301   rksqttgfps  litifsapny  ldvynnkaav  lkyennvmni  rqfncsphpy  wlpnfmdvft
361   wslpfvgekv  temlvnvlsi  csddelmteg  edqfdgsaaa  rkeiirnkir  aigkmarvfs
421   vlreesesvl  tlkgltptgm  lpsgvlaggr  qtlqsatvea  ieaekairgf  spphricsfe
481   eakgldrine  rmpprkdavq  qdgfnslnta  hatenhgtgn  htaq
```

C) <u>Protein phosphatase 3 (formerly 2B), catalytic subunit, gamma isoform (calcineurin A gamma) [Homo sapiens] (accession number NP_005596)</u>

```
  1   msgrrfhlst  tdrvikavpf  pptqrltfke  vfengkpkvd  vlknhlvkeg  rleeevalki
 61   indgaailrq  ektmievdap  itvcgdihgq  ffdlmklfev  ggspsntryl  flgdyvdrgy
121   fsiecvlylw  slkinhpktl  fllrgnhecr  hltdyftfkq  ecrikyseqv  ydacmetfdc
181   lplaallnqq  flcvhggmsp  eitslddirk  ldrfteppaf  gpvcdllwsd  psedygnekt
241   lehythntvr  gcsyfysypa  vceflqnnnl  lsiiraheaq  dagyrmyrks  qatgfpslit
301   ifsapnyldv  ynnkaavlky  ennvmnirqf  ncsphpywlp  nfmdvftwsl  pfvgekvtem
361   lvnvlnicsd  delisddeae  gsttvrkeii  rnkiraigkm  arvfsilrqe  sesvltlkgl
421   tptgtlplgv  lsggkqtiet  atveaveare  airgfslqhk  irsfeeargl  drinermppr
481   kdsihaggpm  ksvtsahsha  ahrsdqgkka  hs
```

Figure 6

NS5ATP2 [Homo sapiens] (accession number AAQ09597)

```
1    masvssatfs ghgarsllqf lrlvgqlkrv prtgwvyrnv qrpesvsdhm yrmavmamvi
61   kddrlnkdrc vrlalvhdma ecivgdiapa dnipkeekhr reeeamkqit qllpedlrke
121  lyelweeyet qssaeakfvk qldqcemilq aseyedlehk pgrlqdfyds tagkfnhpei
181  vqlvseleae rstniaaaas ephs
```

Figure 7

Thioredoxin [Homo sapiens] (accession number NP 003320)

```
1    mvkqieskta fqealdaagd klvvvdfsat wcgpckmikp ffhslsekys nviflevdvd
61   dcqdvasece vkcmptfqff kkgqkvgefs gankekleat inelv
```

Figure 8

R5G42
MVKQIESKTA FQEALDAAGD KLVVVDFSAT WCGPSAVTFA VCALGPCKMI KPFFHSLSEK
YSNVIFLEVD VDDCQDVASE CEVKCMPTFQ FFKKGQKVGE FSGANKEKLE ATINELV

C2
MVKQIESKTA FQEALDAAGD KLVVVDFSAT WCGPSAVTFA VCALGPCKMI K FFHSLSEK
YSNVIFLEVD VDDCQDVASE CEVKCMPTFQ FFKKGQKVGE FSGANKEKLE ATINELV

C3
MVKQIESKTA FQEALDAAGD KLVVVDFSAT WCGPSAVTFA VCALGPCKMI KPFFHSLSE
YSNVIFLEVD VDDCQDVASE CEVKCMPTFQ FFKKGQKVGE FSGANKEKLE ATINELV

C4
MVKQIESKTA FQEALDAAG KLVVVDFSAT WCGPSAVTFA VCALGPCKMI KPFFHSLSEK
YSNVIFLEVD VDDCQDVASE CEVKCMPTFQ FFKKGQKVGE FSGANKEKLE ATINELV

C5
MVKQIESKTA FQEALDAAGD KLVVVDFSAT WCGPSAVTFA VCALGPCKMI KPFFHSLSEE
YSNVIFLEVD VDDCQDVASE CEVKCMPTFQ FFKKGQKVGE FSGANKEKLE ATINELV

C7
MVKQIESKTA FQEALDAAGD K VVVDFSAT WCGPSAVTFA VCALGPCKMI KPFFHSLSEK
YSNVIFLEVD VDDCQDVASE CEVKCMPTFQ FFKKGQKVGE FSGANKEKLE ATINELV

C8
MVKQIESKTA FQEALDAAGD KLVVVDFSAT WCGPSAVT A VCALGPCKMI KPFFHSLSEK
YSNVIFLEVD VDDCQDVASE CEVKCMPTFQ FFKKGQKVGE FSGANKEKLE ATINELV

C12
MVKQIESKTA FQEALDAAGD KLVVVDFSAT WCGPSAVTFA VCALGPCKMI KPFFHSLSEK
YS VIFLEVD VDDCQDVASE CEVKCMPTFQ FFKKGQKVGE FSGANKEKLE ATINELV

N9
MVKQIESKTA FQEALDAAGD KLVVVDFSA WCGPSAVTFA VCALGPCKMI KPFFHSLSEK
YSNVIFLEVD VDDCQDVASE CEVKCMPTFQ FFKKGQKVGE FSGANKEKLE ATINELV

N12
MVKQIESKTA FQEALDAAGD KLVVVDFSAT WC PSAVTFA VCALGPCKMI KPFFHSLSEK
YSNVIFLEVD VDDCQDVASE CEVKCMPTFQ FFKKGQKVGE FSGANKEKLE ATINELV

Figure 12A
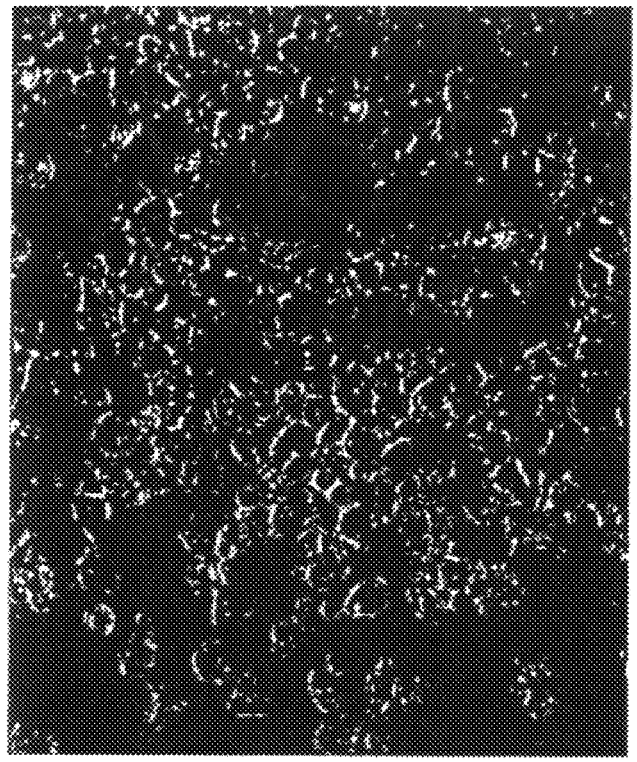
pCI-HA Trx - RANKL
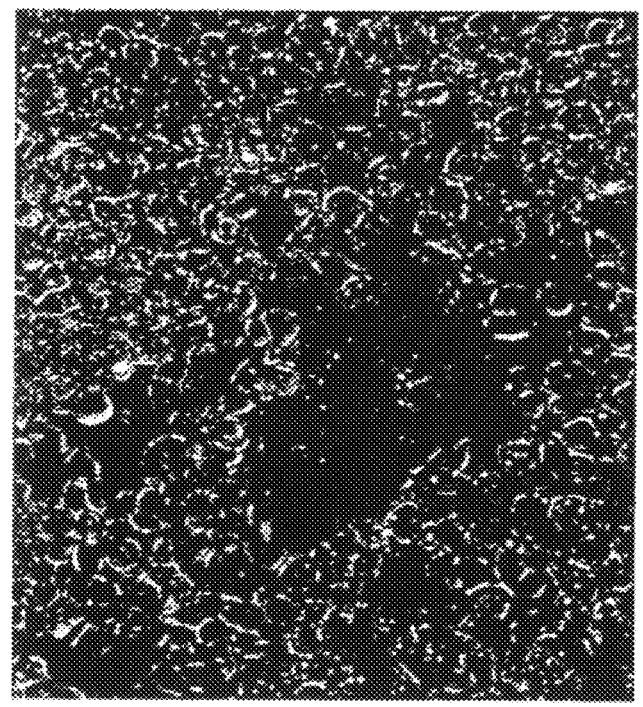
pCI-HA +RANKL

Figure 17

CNA1 (FULL LENGTH)

MAAPEPARAAPPPPPPPPPPPGADRVVKAVPFPPTHRLTSEEVFDLDGIPRVDVLKNHLVKEGRVDEEIALRIINEGAAI
LRREKTMIEVEAPITVCGDIHGQFFDLMKLFEVGGSPANTRYLFLGDYVDRGYFSIECVLYLWVLKILYPSTLFLLRGNH
ECRHLTEYFTFKQECKIKYSERVYEACMEAFDSLPLAALLNQQFLCVHGGLSPEIHTLDDIRRLDRFKEPPAFGPMCDL
LWSDPSEDFGNEKSQEHFSHNTVRGCSYFYNYPAVCEFLQNNNLLSIIRAHEAQDAGYRMYRKSQTTGFPSLITIFSA
PNYLDVYNNKAAVLKYENNVMNIRQFNC

CNA2

MQFNCSPHPYWLPNFMDVFTWSLPFVGEKVTEMLVNVLSICSDDELMTEGEDQFDGSAAARKEIIRNKIRAIGKMARV
FSVLREESESVLTLKGLTPTGMLPSGVLAGGRQTLQSATVEAIEAEKAIRFSPPHRICSFEEAKGLDRINERMPPRKDA
VQQDGFNSLNTAHATENHGTGNHTAQ

CNA3

MDELMTEGEDQFDGSAAARKEIIRNKIRAIGKMARVFSVLREESESVLTLKGLTPTGMLPSGVLAGGRQTLQSATVEAI
EAEKAIRFSPPHRICSFEEAKGLDRINERMPPRKDAVQQDGFNSLNTAHATENHGTGNHTAQ

CNA4

MKMARVFSVLREESESVLTLKGLTPTGMLPSGVLAGGRQTLQSATVEAIEAEKAIRFSPPHRICSFEEAKGLDRINERM
PPRKDAVQQDGFNSLNTAHATENHGTGNHTAQ

CNA5

MKMARVFSVLREESESVLTLKGLTPTGMLPSGVLAGGRQTLQSATVEAIEAEKAIRFSPPHRICSFEEAKGLDRINE

CNA6

AEKAIRFSPPHRICSFEEAKGLDRINERMPPRKDAVQQDGFNSLNTAHATENHGTGNHTAQ

CNA7

MAAPEPARAAPPPPPPPPPPPGADRVVKAVPFPPTHRLTSEEVFDLDGIPRVDVLKNHLVKEGRVDEEIALRIINEGAAI
LRREKTMIEVEAPITVCGDIHGQFFDLMKLFEVGGSPANTRYLFLGDYVDRGYFSIECVLYLWVLKILYPSTLFLLRGNH
ECRHLTEYFTFKQECKIKYSERVYEACMEAFDSLPLAALLNQQFLCVHGGLSPEIHTLDDIRRLDRFKEPPAFGPMCDL
LWSDPSEDFGNEKSQEHFSHNTVRGCSYFYNYPAVCEFLQNNNLLSIIRAHEAQDAGYRMYRKSQTTGFPSLITIFSA
PNYLDVYNNKAAVLKYENNVMNIRQFNCSPHPYWLPNFMDVFTWSLPFVGEKVTEMLVNVLSICSDDELMTEGEDQF
DGSAAARKEIIRNKIRAIG

CNA8 (CONSTITUVELY ACTIVE)

MAAPEPARAAPPPPPPPPPPPGADRVVKAVPFPPTHRLTSEEVFDLDGIPRVDVLKNHLVKEGRVDEEIALRIINEGAAI
LRREKTMIEVEAPITVCGDIHGQFFDLMKLFEVGGSPANTRYLFLGDYVDRGYFSIECVLYLWVLKILYPSTLFLLRGNH
ECRHLTEYFTFKQECKIKYSERVYEACMEAFDSLPLAALLNQQFLCVHGGLSPEIHTLDDIRRLDRFKEPPAFGPMCDL
LWSDPSEDFGNEKSQEHFSHNTVRGCSYFYNYPAVCEFLQNNNLLSIIRAHEAQDAGYRMYRKSQTTGFPSLITIFSA
PNYLDVYNNKAAVLKYENNVMNIRQFNCSPHPYWLPNFMDVFTWSLPFVGEKVTEMLVNVLSICSDDELMT

CNA9

QFNCSPHPYWLPNFMDVFTWSLPFVGEKVTEMLVNVLSICSDDELMTEGEDQFDVGSAAARKEIIRNKIRAIGKMARV

CNA10

DELMTEGEDQFDVGSAAARKEIIRNKIRAIGKMARV

CNA11

DELMTEGEDQFDVGSAAARKEIIRNKIRAIGKMARVFSVLREESESVLTLKGLTPTGMLPSGVLAGGRQTLQSATVEAI
EAEKAIRGFSPPHRICSFEEAKGLDRINERMPP

C

SEQUENCE LISTING

```
<160> NUMBER OF SEQ ID NOS: 45

<210> SEQ ID NO 1
<211> LENGTH: 43
<212> TYPE: DNA
<213> ORGANISM: Artificial
<220> FEATURE:
<223> OTHER INFORMATION: Primer

<400> SEQUENCE: 1
gatcgctaag cgaattcctc gaggcgcgcg tcgaccagga tcc          43

<210> SEQ ID NO 2
<211> LENGTH: 44
<212> TYPE: DNA
<213> ORGANISM: Artificial
<220> FEATURE:
<223> OTHER INFORMATION: Primer

<400> SEQUENCE: 2
agcttggatc ctggtcgacg cgcgcctcga ggaattcgct tagc         44
```

```
<210> SEQ ID NO 3
<211> LENGTH: 33
<212> TYPE: DNA
<213> ORGANISM: Artificial
<220> FEATURE:
<223> OTHER INFORMATION: Primer

<400> SEQUENCE: 3
gcggctaagc catgtaccct tatgatgtgc cag                                    33

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ggagacttga ccaaacctct g                                                 21

<210> SEQ ID NO 5
<211> LENGTH: 74
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (22)..(23)
<223> OTHER INFORMATION: N = A or C or G or T
<220> FEATURE:
<221> NAME/KEY: misc_feature
<222> LOCATION: (25)..(26)
<223> OTHER INFORMATION: N = A or C or G or T
<220> FEATURE:
<221> NAME/KEY: misc_feature
<222> LOCATION: (28)..(29)
<223> OTHER INFORMATION: N = A or C or G or T
<220> FEATURE:
<221> NAME/KEY: misc_feature
<222> LOCATION: (31)..(32)
<223> OTHER INFORMATION: N = A or C or G or T
<220> FEATURE:
<221> NAME/KEY: misc_feature
<222> LOCATION: (34)..(35)
<223> OTHER INFORMATION: N = A or C or G or T
<220> FEATURE:
<221> NAME/KEY: misc_feature
<222> LOCATION: (37)..(38)
<223> OTHER INFORMATION: N = A or C or G or T
<220> FEATURE:
<221> NAME/KEY: misc_feature
<222> LOCATION: (40)..(41)
<223> OTHER INFORMATION: N = A or C or G or T
<220> FEATURE:
<221> NAME/KEY: misc_feature
<222> LOCATION: (43)..(44)
<223> OTHER INFORMATION: N = A or C or G or T
<220> FEATURE:
<221> NAME/KEY: misc_feature
<222> LOCATION: (46)..(47)
<223> OTHER INFORMATION: N = A or C or G or T
<220> FEATURE:
<221> NAME/KEY: misc_feature
<222> LOCATION: (49)..(50)
<223> OTHER INFORMATION: N = A or C or G or T

<400> SEQUENCE: 5
tgggccgagt ggagcggtcc gnnsnnsnns nnsnnsnnsn nsnnsnnsnn cggaccgagc        60
aagatgatcg cccc                                                         74
```

```
<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
ggggcgatca tcttgctcgg tccg                                          24

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
aaccggtgcc tagagaaggt                                               20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
agacccctag gaatgctcgt                                               20

<210> SEQ ID NO 9
<211> LENGTH: 53
<212> TYPE: DNA
<213> ORGANISM: Artificial
<220> FEATURE:
<223> OTHER INFORMATION: Primer RH6

<400> SEQUENCE: 9
ttatgatgtg ccagattatg cctctcccga attcagtatt tgctctgatg atg          53

<210> SEQ ID NO 10
<211> LENGTH: 55
<212> TYPE: DNA
<213> ORGANISM: Artificial
<220> FEATURE:
<223> OTHER INFORMATION: Primer RH4

<400> SEQUENCE: 10
aaacctctgg cgaagaagtc caaagcttct cgagctactg tacagcatct ttccg        55

<210> SEQ ID NO 11
<211> LENGTH: 56
<212> TYPE: DNA
<213> ORGANISM: Artificial
<220> FEATURE:
<223> OTHER INFORMATION: Primer RH3

<400> SEQUENCE: 11
aaacctctgg cgaagaagtc caaagcttct cgagctaggc actttgcagg gtctgc       56

<210> SEQ ID NO 12
<211> LENGTH: 54
<212> TYPE: DNA
<213> ORGANISM: Artificial
<220> FEATURE:
<223> OTHER INFORMATION: Primer RH7
```

-continued

<400> SEQUENCE: 12
acctctggcg aagaagtcca aagcttctcg agtcacctga aacagagaa gact          54

<210> SEQ ID NO 13
<211> LENGTH: 31
<212> TYPE: DNA
<213> ORGANISM: Artificial
<220> FEATURE:
<223> OTHER INFORMATION: Primer

<400> SEQUENCE: 13
gcaagctagc atgtacccatt atgatgtgcc a                                 31

<210> SEQ ID NO 14
<211> LENGTH: 33
<212> TYPE: DNA
<213> ORGANISM: Artificial
<220> FEATURE:
<223> OTHER INFORMATION: Primer

<400> SEQUENCE: 14
cgttgcggcc gcttagacta attcattaat ggt                                33

<210> SEQ ID NO 15
<211> LENGTH: 204
<212> TYPE: PRT
<213> ORGANISM: Homo sapiens

<400> SEQUENCE: 15

Met Ala Ser Val Ser Ser Ala Thr Phe Ser Gly His Gly Ala Arg Ser
1               5                   10                  15

Leu Leu Gln Phe Leu Arg Leu Val Gly Gln Leu Lys Arg Val Pro Arg
            20                  25                  30

Thr Gly Trp Val Tyr Arg Asn Val Gln Arg Pro Glu Ser Val Ser Asp
        35                  40                  45

His Met Tyr Arg Met Ala Val Met Ala Met Val Ile Lys Asp Asp Arg
    50                  55                  60

Leu Asn Lys Asp Arg Cys Val Arg Leu Ala Leu Val His Asp Met Ala
65                  70                  75                  80

Glu Cys Ile Val Gly Asp Ile Ala Pro Ala Asp Asn Ile Pro Lys Glu
                85                  90                  95

Glu Lys His Arg Arg Glu Glu Glu Ala Met Lys Gln Ile Thr Gln Leu
            100                 105                 110

Leu Pro Glu Asp Leu Arg Lys Glu Leu Tyr Glu Leu Trp Glu Glu Tyr
        115                 120                 125

Glu Thr Gln Ser Ser Ala Glu Ala Lys Phe Val Lys Gln Leu Asp Gln
    130                 135                 140

Cys Glu Met Ile Leu Gln Ala Ser Glu Tyr Glu Asp Leu Glu His Lys
145                 150                 155                 160

Pro Gly Arg Leu Gln Asp Phe Tyr Asp Ser Thr Ala Gly Lys Phe Asn
                165                 170                 175

His Pro Glu Ile Val Gln Leu Val Ser Glu Leu Glu Ala Glu Arg Ser
            180                 185                 190

Thr Asn Ile Ala Ala Ala Ala Ser Glu Pro His Ser
        195                 200

<210> SEQ ID NO 16
<211> LENGTH: 521
<212> TYPE: PRT
<213> ORGANISM: Homo sapiens

```
<400> SEQUENCE: 16

Met Ser Glu Pro Lys Ala Ile Asp Pro Lys Leu Ser Thr Thr Asp Arg
1               5                   10                  15

Val Val Lys Ala Val Pro Phe Pro Ser His Arg Leu Thr Ala Lys
                20                  25                  30

Glu Val Phe Asp Asn Asp Gly Lys Pro Arg Val Asp Ile Leu Lys Ala
                35                  40                  45

His Leu Met Lys Glu Gly Arg Leu Glu Ser Val Ala Leu Arg Ile
    50                  55                  60

Ile Thr Glu Gly Ala Ser Ile Leu Arg Gln Glu Lys Asn Leu Leu Asp
65                  70                  75                  80

Ile Asp Ala Pro Val Thr Val Cys Gly Asp Ile His Gly Gln Phe Phe
                85                  90                  95

Asp Leu Met Lys Leu Phe Glu Val Gly Gly Ser Pro Ala Asn Thr Arg
                100                 105                 110

Tyr Leu Phe Leu Gly Asp Tyr Val Asp Arg Gly Tyr Phe Ser Ile Glu
                115                 120                 125

Cys Val Leu Tyr Leu Trp Ala Leu Lys Ile Leu Tyr Pro Lys Thr Leu
130                 135                 140

Phe Leu Leu Arg Gly Asn His Glu Cys Arg His Leu Thr Glu Tyr Phe
145                 150                 155                 160

Thr Phe Lys Gln Glu Cys Lys Ile Lys Tyr Ser Glu Arg Val Tyr Asp
                165                 170                 175

Ala Cys Met Asp Ala Phe Asp Cys Leu Pro Leu Ala Ala Leu Met Asn
                180                 185                 190

Gln Gln Phe Leu Cys Val His Gly Gly Leu Ser Pro Glu Ile Asn Thr
                195                 200                 205

Leu Asp Asp Ile Arg Lys Leu Asp Arg Phe Lys Glu Pro Pro Ala Tyr
210                 215                 220

Gly Pro Met Cys Asp Ile Leu Trp Ser Asp Pro Leu Glu Asp Phe Gly
225                 230                 235                 240

Asn Glu Lys Thr Gln Glu His Phe Thr His Asn Thr Val Arg Gly Cys
                245                 250                 255

Ser Tyr Phe Tyr Ser Tyr Pro Ala Val Cys Glu Phe Leu Gln His Asn
                260                 265                 270

Asn Leu Leu Ser Ile Leu Arg Ala His Glu Ala Gln Asp Ala Gly Tyr
                275                 280                 285

Arg Met Tyr Arg Lys Ser Gln Thr Thr Gly Phe Pro Ser Leu Ile Thr
    290                 295                 300

Ile Phe Ser Ala Pro Asn Tyr Leu Asp Val Tyr Asn Asn Lys Ala Ala
305                 310                 315                 320

Val Leu Lys Tyr Glu Asn Asn Val Met Asn Ile Arg Gln Phe Asn Cys
                325                 330                 335

Ser Pro His Pro Tyr Trp Leu Pro Asn Phe Met Asp Val Phe Thr Trp
                340                 345                 350

Ser Leu Pro Phe Val Gly Glu Lys Val Thr Glu Met Leu Val Asn Val
                355                 360                 365

Leu Asn Ile Cys Ser Asp Asp Glu Leu Gly Ser Glu Glu Asp Gly Phe
                370                 375                 380

Asp Gly Ala Thr Ala Ala Ala Arg Lys Glu Val Ile Arg Asn Lys Ile
385                 390                 395                 400

Arg Ala Ile Gly Lys Met Ala Arg Val Phe Ser Val Leu Arg Glu Glu
                405                 410                 415
```

-continued

Ser Glu Ser Val Leu Thr Leu Lys Gly Leu Thr Pro Thr Gly Met Leu
            420                 425                 430

Pro Ser Gly Val Leu Ser Gly Gly Lys Gln Thr Leu Gln Ser Ala Thr
            435                 440                 445

Val Glu Ala Ile Glu Ala Asp Glu Ala Ile Lys Gly Phe Ser Pro Gln
450                 455                 460

His Lys Ile Thr Ser Phe Glu Glu Ala Lys Gly Leu Asp Arg Ile Asn
465                 470                 475                 480

Glu Arg Met Pro Pro Arg Arg Asp Ala Met Pro Ser Asp Ala Asn Leu
            485                 490                 495

Asn Ser Ile Asn Lys Ala Leu Thr Ser Glu Thr Asn Gly Thr Asp Ser
            500                 505                 510

Asn Gly Ser Asn Ser Ser Asn Ile Gln
            515                 520

<210> SEQ ID NO 17
<211> LENGTH: 524
<212> TYPE: PRT
<213> ORGANISM: Homo sapiens

<400> SEQUENCE: 17

Met Ala Ala Pro Glu Pro Ala Arg Ala Ala Pro Pro Pro Pro Pro Pro
1               5                   10                  15

Pro Pro Pro Pro Gly Ala Asp Arg Val Val Lys Ala Val Pro Phe
            20                  25                  30

Pro Pro Thr His Arg Leu Thr Ser Glu Glu Val Phe Asp Leu Asp Gly
            35                  40                  45

Ile Pro Arg Val Asp Val Leu Lys Asn His Leu Val Lys Glu Gly Arg
50                  55                  60

Val Asp Glu Glu Ile Ala Leu Arg Ile Ile Asn Gly Ala Ala Ile
65                  70                  75                  80

Leu Arg Arg Glu Lys Thr Met Ile Glu Val Glu Ala Pro Ile Thr Val
            85                  90                  95

Cys Gly Asp Ile His Gly Gln Phe Phe Asp Leu Met Lys Leu Phe Glu
            100                 105                 110

Val Gly Gly Ser Pro Ala Asn Thr Arg Tyr Leu Phe Leu Gly Asp Tyr
            115                 120                 125

Val Asp Arg Gly Tyr Phe Ser Ile Glu Cys Val Leu Tyr Leu Trp Val
130                 135                 140

Leu Lys Ile Leu Tyr Pro Ser Thr Leu Phe Leu Leu Arg Gly Asn His
145                 150                 155                 160

Glu Cys Arg His Leu Thr Glu Tyr Phe Thr Phe Lys Gln Glu Cys Lys
            165                 170                 175

Ile Lys Tyr Ser Glu Arg Val Tyr Glu Ala Cys Met Glu Ala Phe Asp
            180                 185                 190

Ser Leu Pro Leu Ala Ala Leu Leu Asn Gln Gln Phe Leu Cys Val His
            195                 200                 205

Gly Gly Leu Ser Pro Glu Ile His Thr Leu Asp Asp Ile Arg Arg Leu
            210                 215                 220

Asp Arg Phe Lys Glu Pro Pro Ala Phe Gly Pro Met Cys Asp Leu Leu
225                 230                 235                 240

Trp Ser Asp Pro Ser Glu Asp Phe Gly Asn Glu Lys Ser Gln Glu His
            245                 250                 255

Phe Ser His Asn Thr Val Arg Gly Cys Ser Tyr Phe Tyr Asn Tyr Pro
            260                 265                 270

```
Ala Val Cys Glu Phe Leu Gln Asn Asn Asn Leu Leu Ser Ile Ile Arg
        275                 280                 285

Ala His Glu Ala Gln Asp Ala Gly Tyr Arg Met Tyr Arg Lys Ser Gln
        290                 295                 300

Thr Thr Gly Phe Pro Ser Leu Ile Thr Ile Phe Ser Ala Pro Asn Tyr
305                 310                 315                 320

Leu Asp Val Tyr Asn Asn Lys Ala Ala Val Leu Lys Tyr Glu Asn Asn
                325                 330                 335

Val Met Asn Ile Arg Gln Phe Asn Cys Ser Pro His Pro Tyr Trp Leu
                340                 345                 350

Pro Asn Phe Met Asp Val Phe Thr Trp Ser Leu Pro Phe Val Gly Glu
        355                 360                 365

Lys Val Thr Glu Met Leu Val Asn Val Leu Ser Ile Cys Ser Asp Asp
370                 375                 380

Glu Leu Met Thr Glu Gly Glu Asp Gln Phe Asp Gly Ser Ala Ala Ala
385                 390                 395                 400

Arg Lys Glu Ile Ile Arg Asn Lys Ile Arg Ala Ile Gly Lys Met Ala
                405                 410                 415

Arg Val Phe Ser Val Leu Arg Glu Glu Ser Glu Ser Val Leu Thr Leu
                420                 425                 430

Lys Gly Leu Thr Pro Thr Gly Met Leu Pro Ser Gly Val Leu Ala Gly
        435                 440                 445

Gly Arg Gln Thr Leu Gln Ser Ala Thr Val Glu Ala Ile Glu Ala Glu
        450                 455                 460

Lys Ala Ile Arg Gly Phe Ser Pro Pro His Arg Ile Cys Ser Phe Glu
465                 470                 475                 480

Glu Ala Lys Gly Leu Asp Arg Ile Asn Glu Arg Met Pro Pro Arg Lys
                485                 490                 495

Asp Ala Val Gln Gln Asp Gly Phe Asn Ser Leu Asn Thr Ala His Ala
                500                 505                 510

Thr Glu Asn His Gly Thr Gly Asn His Thr Ala Gln
        515                 520

<210> SEQ ID NO 18
<211> LENGTH: 512
<212> TYPE: PRT
<213> ORGANISM: Homo sapiens

<400> SEQUENCE: 18

Met Ser Gly Arg Arg Phe His Leu Ser Thr Thr Asp Arg Val Ile Lys
1               5                   10                  15

Ala Val Pro Phe Pro Pro Thr Gln Arg Leu Thr Phe Lys Glu Val Phe
                20                  25                  30

Glu Asn Gly Lys Pro Lys Val Asp Val Leu Lys Asn His Leu Val Lys
        35                  40                  45

Glu Gly Arg Leu Glu Glu Glu Val Ala Leu Lys Ile Ile Asn Asp Gly
    50                  55                  60

Ala Ala Ile Leu Arg Gln Glu Lys Thr Met Ile Glu Val Asp Ala Pro
65                  70                  75                  80

Ile Thr Val Cys Gly Asp Ile His Gly Gln Phe Phe Asp Leu Met Lys
                85                  90                  95

Leu Phe Glu Val Gly Gly Ser Pro Ser Asn Thr Arg Tyr Leu Phe Leu
                100                 105                 110

Gly Asp Tyr Val Asp Arg Gly Tyr Phe Ser Ile Glu Cys Val Leu Tyr
        115                 120                 125
```

Leu Trp Ser Leu Lys Ile Asn His Pro Lys Thr Leu Phe Leu Leu Arg
130                 135                 140

Gly Asn His Glu Cys Arg His Leu Thr Asp Tyr Phe Thr Phe Lys Gln
145                 150                 155                 160

Glu Cys Arg Ile Lys Tyr Ser Glu Gln Val Tyr Asp Ala Cys Met Glu
                165                 170                 175

Thr Phe Asp Cys Leu Pro Leu Ala Ala Leu Leu Asn Gln Gln Phe Leu
            180                 185                 190

Cys Val His Gly Gly Met Ser Pro Glu Ile Thr Ser Leu Asp Asp Ile
        195                 200                 205

Arg Lys Leu Asp Arg Phe Thr Glu Pro Ala Phe Gly Pro Val Cys
210                 215                 220

Asp Leu Leu Trp Ser Asp Pro Ser Glu Asp Tyr Gly Asn Glu Lys Thr
225                 230                 235                 240

Leu Glu His Tyr Thr His Asn Thr Val Arg Gly Cys Ser Tyr Phe Tyr
                245                 250                 255

Ser Tyr Pro Ala Val Cys Glu Phe Leu Gln Asn Asn Asn Leu Leu Ser
            260                 265                 270

Ile Ile Arg Ala His Glu Ala Gln Asp Ala Gly Tyr Arg Met Tyr Arg
        275                 280                 285

Lys Ser Gln Ala Thr Gly Phe Pro Ser Leu Ile Thr Ile Phe Ser Ala
290                 295                 300

Pro Asn Tyr Leu Asp Val Tyr Asn Asn Lys Ala Ala Val Leu Lys Tyr
305                 310                 315                 320

Glu Asn Asn Val Met Asn Ile Arg Gln Phe Asn Cys Ser Pro His Pro
                325                 330                 335

Tyr Trp Leu Pro Asn Phe Met Asp Val Phe Thr Trp Ser Leu Pro Phe
            340                 345                 350

Val Gly Glu Lys Val Thr Glu Met Leu Val Asn Val Leu Asn Ile Cys
        355                 360                 365

Ser Asp Asp Glu Leu Ile Ser Asp Asp Glu Ala Gly Ser Thr Thr
370                 375                 380

Val Arg Lys Glu Ile Ile Arg Asn Lys Ile Arg Ala Ile Gly Lys Met
385                 390                 395                 400

Ala Arg Val Phe Ser Ile Leu Arg Gln Glu Ser Glu Ser Val Leu Thr
                405                 410                 415

Leu Lys Gly Leu Thr Pro Thr Gly Thr Leu Pro Leu Gly Val Leu Ser
            420                 425                 430

Gly Gly Lys Gln Thr Ile Glu Thr Ala Thr Val Glu Ala Val Glu Ala
        435                 440                 445

Arg Glu Ala Ile Arg Gly Phe Ser Leu Gln His Lys Ile Arg Ser Phe
450                 455                 460

Glu Glu Ala Arg Gly Leu Asp Arg Ile Asn Glu Arg Met Pro Pro Arg
465                 470                 475                 480

Lys Asp Ser Ile His Ala Gly Gly Pro Met Lys Ser Val Thr Ser Ala
                485                 490                 495

His Ser His Ala Ala His Arg Ser Asp Gln Gly Lys Lys Ala His Ser
            500                 505                 510

<210> SEQ ID NO 19
<211> LENGTH: 105
<212> TYPE: PRT
<213> ORGANISM: Homo sapiens

<400> SEQUENCE: 19

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
            35                  40                  45

Tyr Ser Asn Val Ile Phe Leu Glu Val Asp Val Asp Cys Gln Asp
    50                  55                  60

Val Ala Ser Glu Cys Glu Val Lys Cys Met Pro Thr Phe Gln Phe Phe
65              70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
                100                 105

<210> SEQ ID NO 20
<211> LENGTH: 10
<212> TYPE: PRT
<213> ORGANISM: Artificial
<220> FEATURE:
<223> OTHER INFORMATION: Peptide Ligand Which Binds to CNA

<400> SEQUENCE: 20

Ser Ala Val Thr Phe Ala Val Cys Ala Leu
1               5                   10

<210> SEQ ID NO 21
<211> LENGTH: 14
<212> TYPE: PRT
<213> ORGANISM: Artificial
<220> FEATURE:
<223> OTHER INFORMATION: Peptide Ligand Which Binds to CNA

<400> SEQUENCE: 21

Gly Pro Ser Ala Val Thr Phe Ala Val Cys Ala Leu Gly Pro
1               5                   10

<210> SEQ ID NO 22
<211> LENGTH: 117
<212> TYPE: PRT
<213> ORGANISM: Artificial
<220> FEATURE:
<223> OTHER INFORMATION: Aptamer R5G42

<400> SEQUENCE: 22

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Ser Ala Val Thr Phe Ala Val Cys Ala Leu Gly Pro Cys Lys
            35                  40                  45

Met Ile Lys Pro Phe Phe His Ser Leu Ser Glu Lys Tyr Ser Asn Val
    50                  55                  60

Ile Phe Leu Glu Val Asp Val Asp Cys Gln Asp Val Ala Ser Glu
65              70                  75                  80

Cys Glu Val Lys Cys Met Pro Thr Phe Gln Phe Phe Lys Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115

<210> SEQ ID NO 23
<211> LENGTH: 117
<212> TYPE: PRT
<213> ORGANISM: Artificial
<220> FEATURE:
<223> OTHER INFORMATION: Aptamer R5G42 mutant C2

<400> SEQUENCE: 23

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Ser Ala Val Thr Phe Ala Val Cys Ala Leu Gly Pro Cys Lys
        35                  40                  45

Met Ile Lys Leu Phe Phe His Ser Leu Ser Glu Lys Tyr Ser Asn Val
    50                  55                  60

Ile Phe Leu Glu Val Asp Val Asp Asp Cys Gln Asp Val Ala Ser Glu
65                  70                  75                  80

Cys Glu Val Lys Cys Met Pro Thr Phe Gln Phe Phe Lys Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115

<210> SEQ ID NO 24
<211> LENGTH: 117
<212> TYPE: PRT
<213> ORGANISM: Artificial
<220> FEATURE:
<223> OTHER INFORMATION: Aptamer R5G42 mutant C3

<400> SEQUENCE: 24

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Ser Ala Val Thr Phe Ala Val Cys Ala Leu Gly Pro Cys Lys
        35                  40                  45

Met Ile Lys Pro Phe Phe His Ser Leu Ser Glu Glu Tyr Ser Asn Val
    50                  55                  60

Ile Phe Leu Glu Val Asp Val Asp Asp Cys Gln Asp Val Ala Ser Glu
65                  70                  75                  80

Cys Glu Val Lys Cys Met Pro Thr Phe Gln Phe Phe Lys Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115

<210> SEQ ID NO 25
<211> LENGTH: 117
<212> TYPE: PRT
<213> ORGANISM: Artificial

<220> FEATURE:
<223> OTHER INFORMATION: Aptamer R5G42 mutant C4

<400> SEQUENCE: 25

Met Val Lys Gln Ile Glu Ser Lys Thr Ala Phe Gln Glu Ala Leu Asp
1               5                   10                  15

Ala Ala Gly Gly Lys Leu Val Val Asp Phe Ser Ala Thr Trp Cys
            20                  25                  30

Gly Pro Ser Ala Val Thr Phe Ala Val Cys Ala Leu Gly Pro Cys Lys
            35                  40                  45

Met Ile Lys Pro Phe Phe His Ser Leu Ser Glu Lys Tyr Ser Asn Val
        50                  55                  60

Ile Phe Leu Glu Val Asp Val Asp Asp Cys Gln Asp Val Ala Ser Glu
65                  70                  75                  80

Cys Glu Val Lys Cys Met Pro Thr Phe Gln Phe Phe Lys Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115

<210> SEQ ID NO 26
<211> LENGTH: 117
<212> TYPE: PRT
<213> ORGANISM: Artificial
<220> FEATURE:
<223> OTHER INFORMATION: Aptamer R5G42 mutant C5

<400> SEQUENCE: 26

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Ser Ala Val Thr Phe Ala Val Cys Ala Leu Gly Pro Cys Lys
            35                  40                  45

Met Ile Lys Pro Phe Phe His Ser Leu Ser Glu Glu Tyr Ser Asn Val
        50                  55                  60

Ile Phe Leu Glu Val Asp Val Asp Asp Cys Gln Asp Val Ala Ser Glu
65                  70                  75                  80

Cys Glu Val Lys Cys Met Pro Thr Phe Gln Phe Phe Lys Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115

<210> SEQ ID NO 27
<211> LENGTH: 117
<212> TYPE: PRT
<213> ORGANISM: Artificial
<220> FEATURE:
<223> OTHER INFORMATION: Aptamer R5G42 mutant C7

<400> SEQUENCE: 27

Met Val Lys Gln Ile Glu Ser Lys Thr Ala Phe Gln Glu Ala Leu Asp
1               5                   10                  15

Ala Ala Gly Asp Lys Pro Val Val Asp Phe Ser Ala Thr Trp Cys
            20                  25                  30

```
Gly Pro Ser Ala Val Thr Phe Ala Val Cys Ala Leu Gly Pro Cys Lys
            35                  40                  45

Met Ile Lys Pro Phe Phe His Ser Leu Ser Glu Lys Tyr Ser Asn Val
 50                      55                  60

Ile Phe Leu Glu Val Asp Val Asp Asp Cys Gln Asp Val Ala Ser Glu
 65                  70                  75                  80

Cys Glu Val Lys Cys Met Pro Thr Phe Gln Phe Phe Lys Lys Gly Gln
                 85                  90                  95

Lys Val Gly Glu Phe Ser Gly Ala Asn Lys Glu Lys Leu Glu Ala Thr
            100                 105                 110

Ile Asn Glu Leu Val
            115

<210> SEQ ID NO 28
<211> LENGTH: 117
<212> TYPE: PRT
<213> ORGANISM: Artificial
<220> FEATURE:
<223> OTHER INFORMATION: Aptamer R5G42 mutant C8

<400> SEQUENCE: 28

Met Val Lys Gln Ile Glu Ser Lys Thr Ala Phe Gln Glu Ala Leu Asp
 1               5                  10                  15

Ala Ala Gly Asp Lys Leu Val Val Asp Phe Ser Ala Thr Trp Cys
            20                  25                  30

Gly Pro Ser Ala Val Thr Ile Ala Val Cys Ala Leu Gly Pro Cys Lys
            35                  40                  45

Met Ile Lys Pro Phe Phe His Ser Leu Ser Glu Lys Tyr Ser Asn Val
 50                      55                  60

Ile Phe Leu Glu Val Asp Val Asp Asp Cys Gln Asp Val Ala Ser Glu
 65                  70                  75                  80

Cys Glu Val Lys Cys Met Pro Thr Phe Gln Phe Phe Lys Lys Gly Gln
                 85                  90                  95

Lys Val Gly Glu Phe Ser Gly Ala Asn Lys Glu Lys Leu Glu Ala Thr
            100                 105                 110

Ile Asn Glu Leu Val
            115

<210> SEQ ID NO 29
<211> LENGTH: 117
<212> TYPE: PRT
<213> ORGANISM: Artificial
<220> FEATURE:
<223> OTHER INFORMATION: Aptamer R5G42 mutant C12

<400> SEQUENCE: 29

Met Val Lys Gln Ile Glu Ser Lys Thr Ala Phe Gln Glu Ala Leu Asp
 1               5                  10                  15

Ala Ala Gly Asp Lys Leu Val Val Asp Phe Ser Ala Thr Trp Cys
            20                  25                  30

Gly Pro Ser Ala Val Thr Phe Ala Val Cys Ala Leu Gly Pro Cys Lys
            35                  40                  45

Met Ile Lys Pro Phe Phe His Ser Leu Ser Glu Lys Tyr Ser Ser Val
 50                      55                  60

Ile Phe Leu Glu Val Asp Val Asp Asp Cys Gln Asp Val Ala Ser Glu
 65                  70                  75                  80

Cys Glu Val Lys Cys Met Pro Thr Phe Gln Phe Phe Lys Lys Gly Gln
                 85                  90                  95
```

```
Lys Val Gly Glu Phe Ser Gly Ala Asn Lys Glu Lys Leu Glu Ala Thr
            100                 105                 110

Ile Asn Glu Leu Val
        115

<210> SEQ ID NO 30
<211> LENGTH: 10
<212> TYPE: PRT
<213> ORGANISM: Artificial
<220> FEATURE:
<223> OTHER INFORMATION: Aptamer variable sequence of R7G11

<400> SEQUENCE: 30

Leu His Leu Ala Gly Arg Gly Trp Glu Asn
1               5                   10

<210> SEQ ID NO 31
<211> LENGTH: 10
<212> TYPE: PRT
<213> ORGANISM: Artificial
<220> FEATURE:
<223> OTHER INFORMATION: Aptamer variable sequence of R5G52

<400> SEQUENCE: 31

Ile Gln Ser Pro Pro Glu Ser Pro Thr Gly
1               5                   10

<210> SEQ ID NO 32
<211> LENGTH: 10
<212> TYPE: PRT
<213> ORGANISM: Artificial
<220> FEATURE:
<223> OTHER INFORMATION: Aptamer Variable sequence of R7G44

<400> SEQUENCE: 32

His Gln Ser Thr Ile Gly Val Ala Glu Phe
1               5                   10

<210> SEQ ID NO 33
<211> LENGTH: 117
<212> TYPE: PRT
<213> ORGANISM: Artificial
<220> FEATURE:
<223> OTHER INFORMATION: Aptamer R5G42 mutant N9

<400> SEQUENCE: 33

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Ala Trp Cys
            20                  25                  30

Gly Pro Ser Ala Val Thr Phe Ala Val Cys Ala Leu Gly Pro Cys Lys
        35                  40                  45

Met Ile Lys Pro Phe Phe His Ser Leu Ser Lys Tyr Ser Asn Val
    50                  55                  60

Ile Phe Leu Glu Val Asp Val Asp Asp Cys Gln Asp Val Ala Ser Glu
65                  70                  75                  80

Cys Glu Val Lys Cys Met Pro Thr Phe Gln Phe Phe Lys Gly Gln
                85                  90                  95

Lys Val Gly Glu Phe Ser Gly Ala Asn Lys Glu Lys Leu Glu Ala Thr
            100                 105                 110

Ile Asn Glu Leu Val
        115
```

```
<210> SEQ ID NO 34
<211> LENGTH: 117
<212> TYPE: PRT
<213> ORGANISM: Artificial
<220> FEATURE:
<223> OTHER INFORMATION: Aptamer R5G42 mutant N12

<400> SEQUENCE: 34

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                20                  25                  30

Ser Pro Ser Ala Val Thr Phe Ala Val Cys Ala Leu Gly Pro Cys Lys
            35                  40                  45

Met Ile Lys Pro Phe Phe His Ser Leu Ser Glu Lys Tyr Ser Asn Val
50                  55                  60

Ile Phe Leu Glu Val Asp Val Asp Cys Gln Asp Val Ala Ser Glu
65                  70                  75                  80

Cys Glu Val Lys Cys Met Pro Thr Phe Gln Phe Lys Lys Gly Gln
                85                  90                  95

Lys Val Gly Glu Phe Ser Gly Ala Asn Lys Lys Leu Glu Ala Thr
            100                 105                 110

Ile Asn Glu Leu Val
        115

<210> SEQ ID NO 35
<211> LENGTH: 345
<212> TYPE: PRT
<213> ORGANISM: Artificial
<220> FEATURE:
<223> OTHER INFORMATION: Peptide CNA1 (full length)

<400> SEQUENCE: 35

Met Ala Ala Pro Glu Pro Ala Arg Ala Ala Pro Pro Pro Pro Pro Pro
1               5                   10                  15

Pro Pro Pro Pro Gly Ala Asp Arg Val Val Lys Ala Val Pro Phe
                20                  25                  30

Pro Pro Thr His Arg Leu Thr Ser Glu Glu Val Phe Asp Leu Asp Gly
            35                  40                  45

Ile Pro Arg Val Asp Val Leu Lys Asn His Leu Val Lys Glu Gly Arg
50                  55                  60

Val Asp Glu Glu Ile Ala Leu Arg Ile Ile Asn Glu Gly Ala Ala Ile
65                  70                  75                  80

Leu Arg Arg Glu Lys Thr Met Ile Glu Val Glu Ala Pro Ile Thr Val
                85                  90                  95

Cys Gly Asp Ile His Gly Gln Phe Phe Asp Leu Met Lys Leu Phe Glu
            100                 105                 110

Val Gly Gly Ser Pro Ala Asn Thr Arg Tyr Leu Phe Leu Gly Asp Tyr
            115                 120                 125

Val Asp Arg Gly Tyr Phe Ser Ile Glu Cys Val Leu Tyr Leu Trp Val
130                 135                 140

Leu Lys Ile Leu Tyr Pro Ser Thr Leu Phe Leu Arg Gly Asn His
145                 150                 155                 160

Glu Cys Arg His Leu Thr Glu Tyr Phe Thr Phe Lys Gln Glu Cys Lys
                165                 170                 175

Ile Lys Tyr Ser Glu Arg Val Tyr Glu Ala Cys Met Glu Ala Phe Asp
            180                 185                 190
```

```
Ser Leu Pro Leu Ala Ala Leu Leu Asn Gln Gln Phe Leu Cys Val His
        195                 200                 205

Gly Gly Leu Ser Pro Glu Ile His Thr Leu Asp Asp Ile Arg Arg Leu
    210                 215                 220

Asp Arg Phe Lys Glu Pro Pro Ala Phe Gly Pro Met Cys Asp Leu Leu
225                 230                 235                 240

Trp Ser Asp Pro Ser Glu Asp Phe Gly Asn Glu Lys Ser Gln Glu His
                245                 250                 255

Phe Ser His Asn Thr Val Arg Gly Cys Ser Tyr Phe Tyr Asn Tyr Pro
            260                 265                 270

Ala Val Cys Glu Phe Leu Gln Asn Asn Asn Leu Leu Ser Ile Ile Arg
        275                 280                 285

Ala His Glu Ala Gln Asp Ala Gly Tyr Arg Met Tyr Arg Lys Ser Gln
    290                 295                 300

Thr Thr Gly Phe Pro Ser Leu Ile Thr Ile Phe Ser Ala Pro Asn Tyr
305                 310                 315                 320

Leu Asp Val Tyr Asn Asn Lys Ala Ala Val Leu Lys Tyr Glu Asn Asn
                325                 330                 335

Val Met Asn Ile Arg Gln Phe Asn Cys
            340                 345

<210> SEQ ID NO 36
<211> LENGTH: 183
<212> TYPE: PRT
<213> ORGANISM: Artificial
<220> FEATURE:
<223> OTHER INFORMATION: Peptide fragment of CNA (CNA2)

<400> SEQUENCE: 36

Met Gln Phe Asn Cys Ser Pro His Pro Tyr Trp Leu Pro Asn Phe Met
1               5                   10                  15

Asp Val Phe Thr Trp Ser Leu Pro Phe Val Gly Glu Lys Val Thr Glu
            20                  25                  30

Met Leu Val Asn Val Leu Ser Ile Cys Ser Asp Asp Glu Leu Met Thr
        35                  40                  45

Glu Gly Glu Asp Gln Phe Asp Gly Ser Ala Ala Arg Lys Glu Ile
    50                  55                  60

Ile Arg Asn Lys Ile Arg Ala Ile Gly Lys Met Ala Arg Val Phe Ser
65                  70                  75                  80

Val Leu Arg Glu Glu Ser Glu Ser Val Leu Thr Leu Lys Gly Leu Thr
                85                  90                  95

Pro Thr Gly Met Leu Pro Ser Gly Val Leu Ala Gly Arg Gln Thr
            100                 105                 110

Leu Gln Ser Ala Thr Val Glu Ala Ile Glu Ala Glu Lys Ala Ile Arg
        115                 120                 125

Phe Ser Pro Pro His Arg Ile Cys Ser Phe Glu Glu Ala Lys Gly Leu
    130                 135                 140

Asp Arg Ile Asn Glu Arg Met Pro Pro Arg Lys Asp Ala Val Gln Gln
145                 150                 155                 160

Asp Gly Phe Asn Ser Leu Asn Thr Ala His Ala Thr Glu Asn His Gly
                165                 170                 175

Thr Gly Asn His Thr Ala Gln
            180
```

<210> SEQ ID NO 37
<211> LENGTH: 141
<212> TYPE: PRT
<213> ORGANISM: Artificial
<220> FEATURE:
<223> OTHER INFORMATION: Peptide fragment of CNA (CNA3)

<400> SEQUENCE: 37

```
Met Asp Glu Leu Met Thr Glu Gly Glu Asp Gln Phe Asp Gly Ser Ala
1               5                   10                  15

Ala Ala Arg Lys Glu Ile Ile Arg Asn Lys Ile Arg Ala Ile Gly Lys
            20                  25                  30

Met Ala Arg Val Phe Ser Val Leu Arg Glu Glu Ser Glu Ser Val Leu
        35                  40                  45

Thr Leu Lys Gly Leu Thr Pro Thr Gly Met Leu Pro Ser Gly Val Leu
    50                  55                  60

Ala Gly Gly Arg Gln Thr Leu Gln Ser Ala Thr Val Glu Ala Ile Glu
65                  70                  75                  80

Ala Glu Lys Ala Ile Arg Phe Ser Pro Pro His Arg Ile Cys Ser Phe
                85                  90                  95

Glu Glu Ala Lys Gly Leu Asp Arg Ile Asn Glu Arg Met Pro Pro Arg
            100                 105                 110

Lys Asp Ala Val Gln Gln Asp Gly Phe Asn Ser Leu Asn Thr Ala His
        115                 120                 125

Ala Thr Glu Asn His Gly Thr Gly Asn His Thr Ala Gln
    130                 135                 140
```

<210> SEQ ID NO 38
<211> LENGTH: 111
<212> TYPE: PRT
<213> ORGANISM: Artificial
<220> FEATURE:
<223> OTHER INFORMATION: Peptide fragment of CNA (CNA4)

<400> SEQUENCE: 38

```
Met Lys Met Ala Arg Val Phe Ser Val Leu Arg Glu Glu Ser Glu Ser
1               5                   10                  15

Val Leu Thr Leu Lys Gly Leu Thr Pro Thr Gly Met Leu Pro Ser Gly
            20                  25                  30

Val Leu Ala Gly Gly Arg Gln Thr Leu Gln Ser Ala Thr Val Glu Ala
        35                  40                  45

Ile Glu Ala Glu Lys Ala Ile Arg Phe Ser Pro Pro His Arg Ile Cys
    50                  55                  60

Ser Phe Glu Glu Ala Lys Gly Leu Asp Arg Ile Asn Glu Arg Met Pro
65                  70                  75                  80

Pro Arg Lys Asp Ala Val Gln Gln Asp Gly Phe Asn Ser Leu Asn Thr
                85                  90                  95

Ala His Ala Thr Glu Asn His Gly Thr Gly Asn His Thr Ala Gln
            100                 105                 110
```

<210> SEQ ID NO 39
<211> LENGTH: 77
<212> TYPE: PRT
<213> ORGANISM: Artificial
<220> FEATURE:
<223> OTHER INFORMATION: Peptide fragment of CNA (CNA5)

```
<400> SEQUENCE: 39

Met Lys Met Ala Arg Val Phe Ser Val Leu Arg Glu Glu Ser Glu Ser
1               5                   10                  15

Val Leu Thr Leu Lys Gly Leu Thr Pro Thr Gly Met Leu Pro Ser Gly
            20                  25                  30

Val Leu Ala Gly Gly Arg Gln Thr Leu Gln Ser Ala Thr Val Glu Ala
        35                  40                  45

Ile Glu Ala Glu Lys Ala Ile Arg Phe Ser Pro His Arg Ile Cys
    50                  55                  60

Ser Phe Glu Glu Ala Lys Gly Leu Asp Arg Ile Asn Glu
65                  70                  75

<210> SEQ ID NO 40
<211> LENGTH: 61
<212> TYPE: PRT
<213> ORGANISM: Artificial
<220> FEATURE:
<223> OTHER INFORMATION: Peptide fragment of CNA (CNA6)

<400> SEQUENCE: 40

Ala Glu Lys Ala Ile Arg Phe Ser Pro Pro His Arg Ile Cys Ser Phe
1               5                   10                  15

Glu Glu Ala Lys Gly Leu Asp Arg Ile Asn Glu Arg Met Pro Pro Arg
            20                  25                  30

Lys Asp Ala Val Gln Gln Asp Gly Phe Asn Ser Leu Asn Thr Ala His
        35                  40                  45

Ala Thr Glu Asn His Gly Thr Gly Asn His Thr Ala Gln
    50                  55                  60

<210> SEQ ID NO 41
<211> LENGTH: 413
<212> TYPE: PRT
<213> ORGANISM: Artificial
<220> FEATURE:
<223> OTHER INFORMATION: Peptide fragment of CNA (CNA7)

<400> SEQUENCE: 41

Met Ala Ala Pro Glu Pro Ala Arg Ala Ala Pro Pro Pro Pro Pro Pro
1               5                   10                  15

Pro Pro Pro Pro Gly Ala Asp Arg Val Val Lys Ala Val Pro Phe
            20                  25                  30

Pro Pro Thr His Arg Leu Thr Ser Glu Glu Val Phe Asp Leu Asp Gly
        35                  40                  45

Ile Pro Arg Val Asp Val Leu Lys Asn His Leu Val Lys Glu Gly Arg
    50                  55                  60

Val Asp Glu Glu Ile Ala Leu Arg Ile Ile Asn Glu Gly Ala Ala Ile
65                  70                  75                  80

Leu Arg Arg Glu Lys Thr Met Ile Glu Val Glu Ala Pro Ile Thr Val
                85                  90                  95

Cys Gly Asp Ile His Gly Gln Phe Phe Asp Leu Met Lys Leu Phe Glu
            100                 105                 110

Val Gly Gly Ser Pro Ala Asn Thr Arg Tyr Leu Phe Leu Gly Asp Tyr
        115                 120                 125

Val Asp Arg Gly Tyr Phe Ser Ile Glu Cys Val Leu Tyr Leu Trp Val
    130                 135                 140

Leu Lys Ile Leu Tyr Pro Ser Thr Leu Phe Leu Leu Arg Gly Asn His
145                 150                 155                 160
```

```
Glu Cys Arg His Leu Thr Glu Tyr Phe Thr Phe Lys Gln Glu Cys Lys
                165                 170                 175

Ile Lys Tyr Ser Glu Arg Val Tyr Glu Ala Cys Met Glu Ala Phe Asp
            180                 185                 190

Ser Leu Pro Leu Ala Ala Leu Leu Asn Gln Gln Phe Leu Cys Val His
        195                 200                 205

Gly Gly Leu Ser Pro Glu Ile His Thr Leu Asp Asp Ile Arg Arg Leu
    210                 215                 220

Asp Arg Phe Lys Glu Pro Pro Ala Phe Gly Pro Met Cys Asp Leu Leu
225                 230                 235                 240

Trp Ser Asp Pro Ser Glu Asp Phe Gly Asn Gly Lys Ser Gln Glu His
                245                 250                 255

Phe Ser His Asn Thr Val Arg Gly Cys Ser Tyr Phe Tyr Asn Tyr Pro
            260                 265                 270

Ala Val Cys Glu Phe Leu Gln Asn Asn Asn Leu Leu Ser Ile Ile Arg
        275                 280                 285

Ala His Glu Ala Gln Asp Ala Gly Tyr Arg Met Tyr Arg Lys Ser Gln
    290                 295                 300

Thr Thr Gly Phe Pro Ser Leu Ile Thr Ile Phe Ser Ala Pro Asn Tyr
305                 310                 315                 320

Leu Asp Val Tyr Asn Asn Lys Ala Ala Val Leu Lys Tyr Glu Asn Asn
                325                 330                 335

Val Met Asn Ile Arg Gln Phe Asn Cys Ser Pro His Pro Tyr Trp Leu
            340                 345                 350

Pro Asn Phe Met Asp Val Phe Thr Trp Ser Leu Pro Phe Val Gly Glu
        355                 360                 365

Lys Val Thr Glu Met Leu Val Asn Val Leu Ser Ile Cys Ser Asp Asp
    370                 375                 380

Glu Leu Met Thr Glu Gly Glu Asp Gln Phe Asp Gly Ser Ala Ala Ala
385                 390                 395                 400

Arg Lys Glu Ile Ile Arg Asn Lys Ile Arg Ala Ile Gly
                405                 410

<210> SEQ ID NO 42
<211> LENGTH: 388
<212> TYPE: PRT
<213> ORGANISM: Artificial
<220> FEATURE:
<223> OTHER INFORMATION: Peptide fragment of CNA (CNA8) (constituvely
      active)

<400> SEQUENCE: 42

Met Ala Ala Pro Glu Pro Ala Arg Ala Ala Pro Pro Pro Pro Pro Pro
1               5                   10                  15

Pro Pro Pro Pro Gly Ala Asp Arg Val Val Lys Ala Val Pro Phe
            20                  25                  30

Pro Pro Thr His Arg Leu Thr Ser Glu Glu Val Phe Asp Leu Asp Gly
        35                  40                  45

Ile Pro Arg Val Asp Val Leu Lys Asn His Leu Val Lys Glu Gly Arg
    50                  55                  60

Val Asp Glu Glu Ile Ala Leu Arg Ile Ile Asn Glu Gly Ala Ala Ile
65                  70                  75                  80

Leu Arg Arg Glu Lys Thr Met Ile Glu Val Glu Ala Pro Ile Thr Val
                85                  90                  95

Cys Gly Asp Ile His Gly Gln Phe Phe Asp Leu Met Lys Leu Phe Glu
            100                 105                 110
```

```
Val Gly Gly Ser Pro Ala Asn Thr Arg Tyr Leu Phe Leu Gly Asp Tyr
            115                 120                 125

Val Asp Arg Gly Tyr Phe Ser Ile Glu Cys Val Leu Tyr Leu Trp Val
130                 135                 140

Leu Lys Ile Leu Tyr Pro Ser Thr Leu Phe Leu Arg Gly Asn His
145                 150                 155                 160

Glu Cys Arg His Leu Thr Glu Tyr Phe Thr Phe Lys Gln Glu Cys Lys
                165                 170                 175

Ile Lys Tyr Ser Glu Arg Val Tyr Glu Ala Cys Met Glu Ala Phe Asp
                180                 185                 190

Ser Leu Pro Leu Ala Ala Leu Leu Asn Gln Gln Phe Leu Cys Val His
            195                 200                 205

Gly Gly Leu Ser Pro Glu Ile His Thr Leu Asp Asp Ile Arg Arg Leu
210                 215                 220

Asp Arg Phe Lys Glu Pro Pro Ala Phe Gly Pro Met Cys Asp Leu Leu
225                 230                 235                 240

Trp Ser Asp Pro Ser Glu Asp Phe Gly Asn Glu Lys Ser Gln Glu His
                245                 250                 255

Phe Ser His Asn Thr Val Arg Gly Cys Ser Tyr Phe Tyr Asn Tyr Pro
                260                 265                 270

Ala Val Cys Glu Phe Leu Gln Asn Asn Asn Leu Leu Ser Ile Ile Arg
            275                 280                 285

Ala His Glu Ala Gln Asp Ala Gly Tyr Arg Met Tyr Arg Lys Ser Gln
290                 295                 300

Thr Thr Gly Phe Pro Ser Leu Ile Thr Ile Phe Ser Ala Pro Asn Tyr
305                 310                 315                 320

Leu Asp Val Tyr Asn Asn Lys Ala Ala Val Leu Lys Tyr Glu Asn Asn
                325                 330                 335

Val Met Asn Ile Arg Gln Phe Asn Cys Ser Pro His Pro Tyr Trp Leu
                340                 345                 350

Pro Asn Phe Met Asp Val Phe Thr Trp Ser Leu Pro Phe Val Gly Glu
            355                 360                 365

Lys Val Thr Glu Met Leu Val Asn Val Leu Ser Ile Cys Ser Asp Asp
370                 375                 380

Glu Leu Met Thr
385

<210> SEQ ID NO 43
<211> LENGTH: 78
<212> TYPE: PRT
<213> ORGANISM: Artificial
<220> FEATURE:
<223> OTHER INFORMATION: Peptide fragment of CNA (CNA9)

<400> SEQUENCE: 43

Gln Phe Asn Cys Ser Pro His Pro Tyr Trp Leu Pro Asn Phe Met Asp
1               5                   10                  15

Val Phe Thr Trp Ser Leu Pro Phe Val Gly Glu Lys Val Thr Glu Met
                20                  25                  30

Leu Val Asn Val Leu Ser Ile Cys Ser Asp Asp Glu Leu Met Thr Glu
                35                  40                  45

Gly Glu Asp Gln Phe Asp Val Gly Ser Ala Ala Ala Arg Lys Glu Ile
            50                  55                  60

Ile Arg Asn Lys Ile Arg Ala Ile Gly Lys Met Ala Arg Val
65                  70                  75
```

```
<210> SEQ ID NO 44
<211> LENGTH: 36
<212> TYPE: PRT
<213> ORGANISM: Artificial
<220> FEATURE:
<223> OTHER INFORMATION: Peptide fragment of CNA (CNA10)

<400> SEQUENCE: 44

Asp Glu Leu Met Thr Glu Gly Glu Asp Gln Phe Asp Val Gly Ser Ala
1               5                   10                  15

Ala Ala Arg Lys Glu Ile Ile Arg Asn Lys Ile Arg Ala Ile Gly Lys
            20                  25                  30

Met Ala Arg Val
        35

<210> SEQ ID NO 45
<211> LENGTH: 112
<212> TYPE: PRT
<213> ORGANISM: Artificial
<220> FEATURE:
<223> OTHER INFORMATION: Peptide fragment of CNA (CNA11)

<400> SEQUENCE: 45

Asp Glu Leu Met Thr Glu Gly Glu Asp Gln Phe Asp Val Gly Ser Ala
1               5                   10                  15

Ala Ala Arg Lys Glu Ile Ile Arg Asn Lys Ile Arg Ala Ile Gly Lys
            20                  25                  30

Met Ala Arg Val Phe Ser Val Leu Arg Glu Glu Ser Glu Ser Val Leu
        35                  40                  45

Thr Leu Lys Gly Leu Thr Pro Thr Gly Met Leu Pro Ser Gly Val Leu
    50                  55                  60

Ala Gly Gly Arg Gln Thr Leu Gln Ser Ala Thr Val Glu Ala Ile Glu
65                  70                  75                  80

Ala Glu Lys Ala Ile Arg Gly Phe Ser Pro Pro His Arg Ile Cys Ser
                85                  90                  95

Phe Glu Glu Ala Lys Gly Leu Asp Arg Ile Asn Glu Arg Met Pro Pro
            100                 105                 110
```

POLYPEPTIDES HAVING MODULATORY EFFECTS ON CELLS

This application is a §371 national stage of PCT International Application No. PCT/EP2007/010422, filed Nov. 30, 2007, and claims priority of European Patent Application No. 06291854.5, filed Dec. 1, 2006, the contents of all of which are hereby incorporated by reference into this application.

The present invention relates to peptides and polypeptides having modulatory effects on cell functions and being capable of binding to Calcineurin and/or to NS5A-TP2. The invention also relates to nucleic acid sequences and vectors encoding these peptides and polypeptides, and to cells comprising said polypeptides, nucleic acid sequences or vectors of the invention, as well as to the use of these peptides, polypeptides, nucleic acid sequences, vectors and cells in therapy. The present invention also relates to a method for modulating calcineurin activity, and to a method for intracellular identification of substances which bind to calcineurin and which modulate the physiological effects of calcineurin, that is which modulate calcineurin dependent cellular pathways. The invention further relates to a method for modulating NS5A-TP2 activity, and to a method for intracellular identification of substances which bind to NS5A-TP2 and which modulate the physiological effects of NS5A-TP2, that is which modulate NS5A-TP2 dependent cellular pathways.

In absence of classical genetics, the deciphering of mammalian regulatory networks rests mostly on the reverse genetics methodology, and particularly on the use of transdominant negative agents such as dominant negative alleles (1), antibodies (2), nucleic acid aptamers (3), peptide aptamers (4), antisense or small interfering RNA (5), and small molecule inhibitors when available (6). In most applications, these agents are designed or selected to specifically target a protein and they are then introduced into cellular or animal models to assess the phenotypic consequences of the targeted perturbation they exert. Another approach consists of constructing large libraries of transdominant agents in retroviral vectors and performing genetic selections or screening to isolate library members that confer given phenotypes. Libraries of antisense cDNAs (7), random fragments of cDNAs (8), ribozymes (9), combinatorial peptides (10), shRNAs (11) have been used successfully to interrogate proteomes and identify new members of mammalian regulatory pathways.

Elaborate experimental schemes have thus been developed and used successfully to identify cytostatic random cDNA fragments (12) and random linear peptides terminally fused to GFP (13). In both cases, a counterselection against dividing cells has been devised and, in the latter case, coupled to a positive screening for cells that do not divide and thus maintain a fluorescent vital dye. Whereas different antiproliferative linear peptides have been isolated, their mechanism of action has not been elucidated so far (13).

Peptide aptamers are man-made combinatorial protein reagents that bind target proteins and can interfere with their function in living cells and organisms (14) (4). They consist of conformationally-constrained random sequence peptide loops (called 'variable regions') displayed by a scaffold protein. They bind their cognate targets with a strong affinity and, usually, a high specificity, which allows them to discriminate between closely related members within a protein family (14), or even between different allelic variants of a given protein (15). So far, peptide aptamers have been mostly selected through yeast two-hybrid screening experiments, for their ability to bind a given target protein. In fewer instances, peptide aptamers have been selected for their ability to confer selectable phenotypes to yeast (16,17) and bacteria (18). Peptide aptamers selected in yeast have been used successfully to identify their cognate target proteins by two-hybrid screening.

A number of arguments strongly support the choice of peptide aptamers to perform various phenotypic screening or selections, with the goal of interrogating proteomes to identify target proteins involved in the underlying regulatory networks. First, proof of concept has been obtained in yeast where peptide aptamers were selected for their ability to overcome the cell cycle arrest induced by a mating pheromone, and where target proteins were identified by yeast two-hybrid screening (16,17). Second, peptide aptamers can target many different kinds of intracellular proteins such as kinases, phosphatases, receptors, adaptor proteins, transcription factors, chaperones, etc., involved in many regulatory pathways (reviewed in (4)). Third, peptide aptamers have been shown to decorate their target proteins by binding to many different surfaces, involved in different functions (27). For this reason, peptide aptamers can induce a wider range of perturbations on protein function than other reverse genetics methods, such as gene knockout or the use of transdominant negative alleles. Last, the double constraint imposed on the variable regions reduces the conformational freedom and yields typically high binding affinities for the target proteins, thereby facilitating their identification by different methods.

The work of the inventors illustrates the particularities of using combinatorial protein molecules for phenotypic screening of transdominant reagents, as opposed to using nucleic acid molecules. For example, when using nucleic acid molecules (cDNA fragments, antisense, shRNAs), the identity of the target proteins is immediately unveiled by sequencing the isolated library members. In contrast, selected combinatorial protein molecules must be used as probes to determine the identity of their targets, by performing yeast two-hybrid cDNA screening (10,16,17) or affinity capture experiments followed by mass spectrometry (28).

However, combinatorial protein molecules, and particularly peptide aptamers, present a considerable advantage over nucleic acid molecules. Whereas the latter can only inhibit the function of their target proteins (by a dominant negative effect or by reducing expression levels), the former can cause more diverse perturbations on the function of their targets, including an activation as observed in the present invention. Therefore, the use of combinatorial protein molecules for phenotypic screening or selections allows a more extensive probing of proteomes, thus enhancing the chances to identify different target proteins whose perturbations cause a given phenotype. Another significant advantage of using peptide aptamers lies in their application for drug discovery. Once their target proteins are identified, peptide aptamers can guide the identification of small molecule mimicks that bind the same molecular surfaces on the targets and induce the same biological effects (27). The use of retroviral libraries of peptide aptamers for phenotypic screening or selections thus aids the unraveling of molecular regulatory networks that control major biological processes and impacts positively on therapeutic research by facilitating the discovery of new targets and small molecule drugs.

In the context of the present invention, the inventors have built and used a lentiviral peptide aptamer library to isolate aptamers that inhibit cell proliferation in vitro. They have determined the identity of the target proteins of one of the isolated peptide aptamers (referred to as R5G42 (SEQ ID 22)) by performing yeast two-hybrid screening experiments (see table 2), and have retained NS5A-TP2 (which contains a conserved HD domain, found in many phosphatases) and CNA (the catalytic subunit of calcineurin), as two strong target candidates. With respect to the first of these targets, no biological information is currently available for NS5A-TP2 (SEQ ID 15), except that its coding gene is transactivated by the non-structural NS5A protein from hepatitis C virus (22). The use of the R5G42 peptide aptamer could help elucidate the function of this protein, which could play a role in the control of cell proliferation.

With respect to the second target, calcineurin (also referred to as protein phosphatase 3 (PPP3) or protein phosphatase 2B (PP2B)) is a well-studied protein phosphatase that plays a key role in coupling $Ca^{2+}$ signaling to cellular responses (reviewed in (23)). Calcineurin is a serine/threonine protein phosphatase constituted of a catalytic subunit, Calcineurin A (CNA) and a $Ca^{2+}$ regulatory unit, Calcineurin B (CNB).

CNA comprises a catalytic domain at its N terminal and a regulatory domain at its C terminal which contains the CNB binding domain, a Calmodulin (CaM) binding domain and an Auto-Inhibitory domain (AI) which masks the active site of CNA (see FIG. 3b). Binding of $Ca^{2+}$ activated calmodulin to CNA displaces the auto-inhibitory domain and activates calcineurin phosphatase activity through the relief of auto-inhibition. Three isoforms of human CNA, referred to as CNA alpha (SEQ ID 16), CNA beta (SEQ ID 17) and CNA gamma (SEQ ID 18), have been identified (see FIG. 5). These three isoforms show from 83 to 89% identity over 90% of their sequence not including the N- and C-terminal tails.

Calcineurin is believed to be involved in many physiological pathways such as T-cell activation, cell apoptosis, skeletal myocyte differentiation, osteoclast differentiation and cardiac hypertrophy. In T-cells, it has been shown that activated CNA dephosphorylates the NFAT (nuclear factor of activated T cell) transcription factor, allowing it to enter the nucleus and activate the transcription of interleukin 2 (IL-2). NFAT is a general name applied to a family of transcription factors which consists of five members, four of which (NFATc1-NFATc4) have been shown to be regulated by $Ca^{2+}$ and Calcineurin. Upon stimulation, NFAT proteins are dephosphorylated by calcineurin, which allows them to translocate to the nucleus and become transcriptionally active (reviewed in (29). NFAT members are involved in the activation or repression of many genes involved in diverse physiological pathways such as T cell activation, the development of cardiac muscle, skeletal muscle cells differentiation, skeletal muscle hypertrophy and the development of nervous systems.

The demonstration that calcineurin was the target of the immunosuppressants cyclosporin A and FK506 has sparked a considerable interest in this protein and has greatly facilitated the elucidation of its function, especially in T cell activation. However, the structural mechanisms of the activation and the inhibition of calcineurin by, respectively, calmodulin and immunophilin-immunosuppressant complexes remain poorly understood (26).

Despite numerous studies, the role of calcineurin in cell proliferation remains less clear. Cyclosporin A has been shown to inhibit the proliferation of various cells, but at concentrations exceeding that required to observe an inhibition of T cell activation. FK506, although a more potent immunosuppressant than cyclosporin A, shows a weaker antiproliferative activity (reviewed in (24)). These observations suggest that the antiproliferative activity of these immunophilins may be caused by the modulation of other target protein(s). Moreover, contrary to the hypothesis that calcineurin positively regulates cell proliferation, calcineurin has been shown to induce apoptosis through different mechanisms including the dephosphorylation of Bad, a pro-apoptotic Bcl-2 family member (25).

In the context of the present invention, the inventors have identified a new CNA ligand that activates CNA phosphatase activity through a potentially original mechanism, since its binding site is located between the CaM-binding domain and the auto-inhibitory domain, but does not appear to be circumscribed to the CaM-binding domain. In accordance with the invention, the new ligand comprises a peptide having the sequence SAVTFAVCAL (SEQ ID 20), or derivatives thereof. The invention thus relates to this peptide, and to larger peptides or polypeptides containing the SAVTFAVCAL sequence, especially to peptide aptamers which contain the SAVTFAVCAL sequence as a conformationally-constrained loop in a protein platform. The invention further relates to the use of the peptide or its derivatives to bring about phenotypic change in eukaryotic cells, in particular in mammalian cells, particularly to up-regulate calcineurin activity.

This application describes the first phenotypic selection of peptide aptamers in mammalian cells. It also describes the first identification of a functional perturbation of a protein targeted by combinatorial protein molecules isolated from an antiproliferative screening.

More specifically, the invention relates to a polypeptide comprising or consisting of
  (i) the amino acid sequence SAVTFAVCAL (SEQ ID 20), or
  (ii) the amino acid sequence GPSAVTFAVCALGP (SEQ ID 21), or
  (iii) a variant of the amino acid sequence (i) or (ii) having one amino acid change.

According to the invention the term polypeptide signifies an amino acid sequence of 9 or more amino acids. Polypeptides consisting exclusively of amino acid sequences (i), (ii) or (iii) as defined above are also referred to herein as peptides of the invention.

The polypeptides of the invention are capable of binding to intracellular molecular targets in eukaryotic cells, in particular in mammalian cells. The binding of the polypeptides of the invention to their intracellular target has a modulatory effect on the cell. Such targets include Calcineurin and/or NS5A-TP2. The interaction of the polypeptide with its target gives rise to a phenotypic change in the cell for example an antiproliferative activity, an apoptic effect or a differentiating effect on mammalian cells.

In a preferred embodiment, the polypeptides of the invention bind to proteins which comprise at least the sequence extending from amino acid 378 to 500 of the beta isoform of CNA, or analogous positions in the alpha and gamma isoforms. In another preferred embodiment, the polypeptides of the invention bind to native CNA, i.e. as occurring in mammalian cells or human cells, more particularly, free of two-hybrid reporter components.

The princeps peptide of the invention is the decapeptide (i):

SAVTFAVCAL (SEQ ID 20)

According to the invention, this decapeptide may be extended at the amino and/or carboxy termini by the addition of further amino acids, for example from one to 300 amino acids, preferably one to 80 amino acids, at either or both sides. The peptide (ii), having 14 amino acids and having the sequence:

GPSAVTFAVCALGP (SEQ ID 21)

is a particularly preferred embodiment of the invention in this regard.

The invention also encompasses variants of the peptides (i) and (ii) having one amino acid difference with respect to the peptide (i) or (ii), wherein 'difference' (or 'change') signifies the substitution, deletion or insertion of one amino acid in the parental sequence (i) or (ii). Said variants are referred to herein as sequence (iii).

Particularly preferred peptide variants (iii) of the invention are those in which one amino acid in the parental sequence (i) or (ii) is substituted by a different amino acid, for example by an amino acid sharing a same property such as polarity, acidity, basicity or hydrophobicity. In one embodiment, one amino acid in the in the C-terminal portion of the (i) or (ii) sequence is substituted by another amino acid. In a preferred embodiment, the substituted amino acid is neither the serine nor one of the two valine amino acids of the (i) or (ii) parental sequence. In a most preferred embodiment, the phenylalanine amino acid is substituted by an isoleucine amino acid.

According to the invention, the amino acid sequence (i), (ii) or (iii) may be part of a larger polypeptide i.e. covalently joined at its amino and/or carboxy termini to other amino acid residues or sequences thereof. For example, the amino acid sequence (i), (ii) or (iii) may be embedded within a larger polypeptide, or may be fused at one or both extremities to a heterologous polypeptide, giving rise to a fusion protein. The total length of such a chimeric polypeptide, including the amino acid sequence (i), (ii) or (iii), is normally from 14 to 600 amino acids, for example 14 to 150 amino acids.

According to a preferred embodiment, the amino acid sequence (i), (ii) or (iii) is conformationally constrained by covalent binding to a scaffold molecule, preferably at both C and N termini, i.e. the sequence (i), (ii) or (iii) is doubly constrained. The scaffold (also called 'platform') can be any molecule which is capable of reducing, through covalent bonding, the number of conformations which the sequence (i), (ii) or (iii) can assume. Examples of conformation-constraining scaffolds include proteins and peptides, for example thioredoxin and thioredoxin-like proteins, nucleases (e.g. RNaseA), proteases (e.g. trypsin), protease inhibitors (e.g. eglin C), antibodies or structurally-rigid fragments thereof, fluorescent proteins such as GFP or YFP, and conotoxins. A conformation-constraining protein or peptide can be of any appropriate length, for example from 5 to 150 amino acids, preferably 5 to 40 or 5 to 60 or 80-120 amino acids. Other suitable platform molecules include carbohydrates such as sepharose. The platform may be a linear or circular molecule, for example, closed to form a loop. The combinatorial constraint may also be bought about by covalent bonding of the N- and C-terminal amino acids of the peptide to each other. The amino acid sequence (i), (ii) or (iii) may e part of a peptide aptamer.

The platform is generally heterologous with respect to the amino acid sequence (i), (ii) or (iii), i.e. the platform is not of the same origin as the amino acid sequence (i), (ii) or (iii).

The association of the platform and amino acid sequence (i), (ii) or (iii) generally does not exist in nature. In particular, the association of the platform and amino acid sequence (i), (ii) or (iii) is preferably not an aquaporin 7 molecule.

According to a preferred embodiment, the scaffold is a protein and the amino acid sequence (i), (ii) or (iii) is located between two cysteines in the scaffold protein. In this manner, the amino acid sequence (i), (ii) or (iii) and any flanking amino acids form a conformationally constrained loop structure which has proven to be particularly suitable as an intracellular recognition molecule.

Human thioredoxin (hTRX) (SEQ ID 19) or E. coli thioredoxin A (TRX-A), or a thioredoxin-like molecule (TRX-like), are particularly preferred as scaffolds. In this case, the amino acid sequence (i), (ii) or (iii) is located in the active-site loop, between the two cysteines at positions 32 and 35 (see amino acid sequence of human thioredoxin illustrated in FIG. 7), or analogous positions in thioredoxin-like (TRX-like) molecules. Thioredoxin-like proteins are defined herein as proteins having at least 50%, preferably at least 80% and most preferably at least 90% identity, for example 95% identity, with the amino acid sequence of human thioredoxin (SEQ ID 19) over an amino acid sequence length of 80 amino acids (see FIG. 7). Thioredoxin-like molecules also include peptides which have a three-dimensional structure substantially similar to that of human or E. coli thioredoxin, for example glutaredoxin. A particularly preferred thioredoxin platform is native human thioredoxin (SEQ ID 19), or alternatively, human thioredoxin having one or more point mutations in the amino acid sequence flanking the active site. In particular, thioredoxin molecules in which one, two or three amino acids of the native human sequence are substituted by different amino acids, are especially suitable as scaffolds of the invention. Indeed, the inventors have demonstrated that the binding affinity of the polypeptide to its intracellular target can be modulated by variation of the amino acid sequence of the human TRX (SEQ ID 19).

In a preferred embodiment, thioredoxin molecules in which one amino acid of the native hTRX sequence is substituted by a different amino acid, are used as scaffolds for the polypeptides of the invention. Particularly preferred variants of human thioredoxin are those in which one amino acid is substituted by a different amino acid, for example by an amino acid sharing a same property such as polarity, acidity, basicity or hydrophobicity.

Alternatively, one amino acid is substituted by a different amino acid having a different polarity, acidity, basicity or hydrophobicity. In a preferred embodiment, the substituted amino acid is neither one of the five amino acids on the amino-side of the cysteine at position 32, nor one of the five amino acids on the carboxy-side of the cysteine at position 35 of hTRX. In yet another preferred embodiment, the substituted amino acid is one of the five amino acids on the amino-side of the cysteine at position 32, or one of the five amino acids on the carboxy-side of the cysteine at position 35 of hTRX.

In a most preferred embodiment, the polypeptide of the invention has one of the sequences listed in FIG. 8 (SEQ ID No 22-29, 33 or 34).

The amino acid sequences (i), (ii) or (iii), when conformationally constrained within a platform such as h-TRX or TRX-like proteins will be referred to herein as peptide aptamers.

According to a preferred embodiment of the invention, the polypeptide is capable of binding to Calcineurin and/or to NS5A-TP2. In one embodiment the polypetides of the invention are capable of binding to CNA and NS5A-TP2. In another embodiment, they are capable of binding to CNA but not to NS5A-TP2. In yet a further embodiment, they are capable of binding to NS5A-TP2 but not to CNA.

In this context, unless otherwise specified, "calcineurin" or "CNA" signifies full length Calcineurin A (human) or a polypeptide comprising at least amino acids 378 to 500 of the beta isoform of human CNA.

"Binding" signifies non-covalent interaction between the polypeptide and Calcineurin and/or NS5A-TP2, sufficient to give rise to a detectable transcriptional signal in a two-hybrid assay. Affinity of binding is generally between $10^{-6}$M and $10^{-9}$M.

Intracellular binding between the polypeptide of the invention and calcineurin and/or NS5A-TP2 can be determined for example by perfoming a two-hybrid (2H) assay, as described in WO 96/02561, in which the polypeptide is the bait protein and calcineurin or NS5A-TP2 is the prey protein. Alternatively calcineurin or NS5A-TP2 can be the bait and the polypeptide can be the prey.

The two-hybrid assay uses the activation of a reporter gene by the binding of a reconstituted transcription factor onto its operator sequences, and the fact that in most eukaryotic transcription factors, the activating and binding domains are modular and can function in close proximity to each other without direct binding. This means that even when the transcription factor is split into two fragments, it can still activate transcription when the two fragments are indirectly connected.

In yeast two-hybrid screening, separate bait and prey plasmids are simultaneously introduced into the mutant yeast strain. Bait plasmids are engineered to produce a protein product in which the binding domain (BD) fragment is fused onto the bait protein. Prey plasmids are engineered to produce a protein product in which the activating domain (AD) fragment is fused onto the prey protein. After transfection of the yeast with both plasmids, interaction between the bait and the prey protein activates the transcription of the reporter gene, and thereby allows the interaction to be detected.

Common transcription factors used for yeast two-hybrid screening include GAL4 and the DNA-binding domain of the *E. coli* protein LexA.

In one embodiment, reporter genes can encode for enzymes that allow synthesis of specific amino acids that the mutant yeast strain is otherwise unable to produce, such as for example leucine and adenine. Thus, yeast containing a bait protein and a prey protein which interact, will grow on media lacking those amino acids.

Another commonly used reporter gene is lacZ which when activated results in yeast colonies that generate a blue colour under certain conditions.

Extracellular or in vitro binding between the polypeptide of the invention and calcineurin and/or NS5A-TP2 can be determined by classical methods analogous to those used for immunodetection, for example, by immobilising the polypeptide on a support and contacting with labelled calcineurin or NS5A-TP2. Alternatively calcineurin or NS5A-TP2 can be immobilised on a support and contacted with the polypeptides of the invention carrying a detectable label.

The polypeptides of the invention generally bind to calcineurin through said amino acid sequence (i), (ii) or (iii), and preferably bind to the calcineurin subunit A. They generally bind to at least one, and preferably all of the alpha (SEQ ID 16), beta (SEQ ID 17) or gamma (SEQ ID 18) isoforms of human calcineurin A (CNA) (see FIG. 5).

The polypeptides of the invention preferably bind to CNA at a site, or at a plurality of sites, located within the sequence extending from the amino terminal of the calmodulin binding domain to the carboxy terminal of the auto-inhibitory domain of CNA (see FIG. 3b). The site is however not limited to the calmodulin binding domain, as this domain is not in itself sufficient for binding.

The polypeptides generally binds to the human CNA beta isoform at its C-terminal through a site, or at a plurality of sites, located within the sequence extending from amino acid 378 to 500, or analogous positions in the alpha and gamma isoforms.

The polypeptide of the invention also generally binds to NS5A-TP2 (SEQ ID 15) (see FIG. 6). The precise binding site of the polypeptide to NS5A-TP2 has not been determined by the inventors.

The polypeptide of the invention are capable of exerting a modulatory effect on a cell, for example at least one cellular function is upregulated, downregulated, activated or eliminated, for example calcineurin-dependent pathways or NS5A-TP2 dependent pathways. Most preferably, the peptides and peptide aptamers of the invention give rise to a specific detectable phenotype or change in phenotype on binding to the target within a cell. For example, the specific detectable phenotype consists in the expression of a reporter gene, a modification of the proliferative rate of the cells, cell apoptosis, a modification of cell differentiation or resistance to cell death. In a preferred embodiment, the polypeptides of the invention have a differentiating effect on osteoclasts in the absence of RANKL, i.e. the polypeptides of the invention enhance the formation of osteoclasts in the absence of RANKL. In another preferred embodiment, the polypeptides of the invention reduce muscular atrophy, indicating enhancement of muscle differentiation.

Most preferably, the specific detectable phenotype brought about by the binding of the polypeptide of the invention to its target, is an antiproliferative activity in mammalian cells, particularly in human cells.

The antiproliferative activity can for example be detected by infecting the cells labelled with the fluorescent vital dye CMTMR which cells incorporate and dilute as they proceed through division cycles, with a lentiviral vector encoding the polypeptide of the invention in conditions in which the polypeptide is expressed in the cells. The cells which do not divide or divide at a slower rate maintain a higher fluorescence level which can be detected, for example by flow cytometry (see FIG. 2A).

Alternatively, antiproliferative activity can be detected by transfecting the cells with a plasmid encoding the polypeptide of the invention in conditions in which the polypeptide is expressed in the cells, cultivating the cells for a period during which they would normally form detectable colonies, for example one to three weeks, detecting the colonies for example by staining of the cells that grow with crystal violet and counting the colonies (see FIG. 2B).

The invention also relates to a nucleic acid sequence comprising or consisting of a sequence encoding the polypeptide of the invention as defined above, and to a vector containing this nucleic acid sequence. Preferably, the vector is suitable for introduction and expression of the nucleic acid in mammalian cells, in mammalian tissue, such as muscle tissue, or in a mammalian organ, for example a retroviral vector, a lentiviral vector or a plasmid.

The invention also encompasses a eukaryotic cell comprising the polypeptide of the invention as defined above, particularly a mammalian cell, or mammalian cell line, for example a murine or human cell or cell line. Particularly preferred cell types are cells of the immune system, skeletal muscle cells, bone cells or cardiac muscle cells, for example T cells, myocytes, satellite cells, muscle fibers, osteoclasts, or osteoblasts.

The polypeptide of the invention may be introduced into the cell in a number of different ways. For example, it can be introduced into the cell by expression of a DNA sequence encoding the polypeptide. This method is generally applied when genetic manipulation of the cell or the organism is possible. In such cases a nucleic acid molecule encoding the polypeptide is introduced into the cell in a suitable vector, comprising all the necessary control sequences for expression.

Alternatively, the polypeptide is introduced into the cell in purified form using a cell permeable agent, such as protein transduction domains (PTDs), for example penetratin.

This method is particularly advantageous for therapy when genetic modification of the individual is undesirable. A further alternative is to microinject the polypeptide into the cell.

The invention also relates to methods for identifying substances which modulate the interaction between calcineurin (CNA) and a polypeptide of the invention. These methods allow the identification of molecules which can up- or down-regulate the physiological effects of calcineurin, and which consequently have therapeutic potential, for example the molecules may up-regulate the phosphatase activity of calcineurin. In particular, these methods allow the identification of molecules which can modulate NFAT-dependent activation or repression of gene transcription.

More particularly, the invention relates to a method for the identification of substances which modulate the interaction between CNA and a polypeptide of the invention, said method comprising the steps of
- (i) contacting a candidate modulatory substance with CNA and the polypeptide of the invention in conditions in which CNA and said polypeptide can bind, and in which said binding can be detected by a specific signal;
- (ii) detecting a change in the intensity of said signal; and
- (iii) optionally recovering the candidate substance.

More specifically, this aspect of the invention includes a method for the identification of substances which modulate the interaction between CNA and a polypeptide of the invention, said method comprising the steps of
- (i) introducing a candidate modulatory substance, CNA and the polypeptide of the invention into a eukaryotic cell, in conditions in which a specific detectable phenotype associated to the binding of CNA with the polypeptide of the invention can be detected;
- (ii) detecting a change of the said specific detectable phenotype; and
- (iii) optionally recovering the candidate substance.

Modulatory substances or ligands identified by this method may be proteins, peptides, small organic molecules, nucleic acids, including DNA or RNA. Small organic molecule can be defined as non polymeric organic molecules which have a molecular weight of less than 3000 Da, preferably less than 2500, 2000, 1500, 1000, 750 or 500 Da.

The interaction which is modulated by the candidate substance is generally the binding of the polypeptide of the invention to CNA at a site or a plurality of sites located within the sequence extending from the amino terminal of the calmodulin binding domain up to and including the carboxy terminal of the auto-inhibitory domain of CNA, particularly, the sequence extending from amino acid 378 to 500 of the beta isoform of CNA, or equivalent positions in the alpha or gamma isoforms. The method of the invention therefore allows identification of molecules which compete with the polypeptide of the invention for this binding site. Such molecules may agonise or antagonise the effect of the polypeptide of the invention, for example they may stimulate or prevent the polypeptide of the invention from stimulating the phosphatase activity of calcineurin, and may stimulate or inhibit the anti-proliferative effect of calcineurin.

The method relies on the detection of a change in the phenotypic status of the cells in the presence of the three components of the system (i.e. the candidate compound, CNA and the polypeptide of the invention), compared to the phenotypic status of the same cells when only CNA and the polypeptide of the invention are introduced into the cells.

The specific detectable phenotype may consist of the expression of a heterologous or endogenous reporter gene, a modification of the proliferative rate of the cells, cell apoptosis, a modification of cell differentiation or resistance to cell death.

The two hybrid assay as described in EP1582590 may be used to identify candidate modulatory substances. In this context, the bait is usually Calcineurin, bound to a DNA-binding moiety, and the prey is usually the polypeptide of the invention, bound to a gene activating moiety. This type of assay allows the identification of substances which modulate binding of the polypeptide of the invention to CNA, as seen by enhancement or inhibition of reporter gene expression. The reporter gene in this context is usually a heterologous reporter gene introduced into the cells for the purpose of the assay.

If it is desired to identify substances which have the capacity to modulate, not only the binding of the polypeptide of the invention to CNA, but also the physiological effect on the cells of this binding, then a phenotypic screen using endogenous cellular phenotypes should be used. For this type of assay, phenotypic characteristics such as expression of an endogenous reporter gene, modification of the proliferative rate of the cells, cell apoptosis, a modification of cell differentiation or resistance to cell death may be used as the readout for modulatory activity.

The invention also relates to methods for identifying substances which modulate the interaction between NS5A-TP2 and a polypeptides according of the invention.

In particular, the invention relates to a method for the identification of substances which modulate the interaction between NS5A-TP2 and a polypeptide of the invention, said method comprising the steps of
- (i) contacting a candidate modulatory substance with NS5A-TP2 and the polypeptide of the invention in conditions in which NS5A-TP2 and said polypeptide can bind, and in which said binding can be detected by a specific signal;
- (ii) detecting a change in the intensity of said signal; and
- (iii) optionally recovering the candidate substance.

More specifically, this aspect of the invention includes a method for the identification of substances which modulate the interaction between NS5A-TP2 and a polypeptide of the invention, said method comprising the steps of
- (i) introducing a candidate modulatory substance, NS5A-TP2 and the polypeptide of the invention into a eukaryotic cell, in conditions in which a specific detectable phenotype associated to the binding of NS5A-TP2 with the polypeptide of the invention can be detected;
- (ii) detecting a change of the said specific detectable phenotype; and
- (iii) optionally recovering the candidate substance.

Molecules which bind to calcineurin at the same site as that bound by the polypeptides of the invention (within the sequence extending from amino acid 378 to 500 of the beta isoform of CNA, or equivalent positions in the alpha or gamma isoforms), may be used to modulate calcineurin activity in vivo or in vitro. Such a method comprises contacting calcineurin with a ligand capable of binding to calcineurin at a site located within the sequence extending from the amino terminal of the calmodulin binding domain to the carboxy terminal of the auto-inhibitory domain of CNA, in conditions suitable to allow effective binding between the ligand and calcineurin thereby modulating at least one activity of calcineurin, for example phosphatase activity, and the consequent anti-proliferative activity. According to this aspect of the invention the ligand may be a polypeptide according to the invention, comprising or consisting of the amino acid sequences (i) (ii) or (iii), or may be a small molecule, nucleic acid or protein which binds to calcineurin at the same site as the polypeptide of the invention.

The polypeptides of the invention can be used as therapeutic agents for use in humans or animals, more particularly as the active ingredient in pharmaceutical compositions, optionally associated with a pharmaceutically acceptable carrier. The nucleic acids encoding the polypeptides of the invention may also be used as therapeutic agents. A particularly preferred embodiment is the use of a peptide (i), (ii) or (iii) of the invention in a TRX or TRX-like scaffold, particularly a human TRX scaffold, as a therapeutic agent. In particular, the invention relates to methods for treating or preventing conditions in which the up-regulation of calcineurin phosphatase activity or the activation of NS5A-TP2 is required, by administering to an individual in need of such treatment, effective amounts of the polypeptide or nucleic acid of the invention. Preferably, the administration is performed at the body site or organ concerned by the pathology, for example muscle, bone, brain, heart, etc.

One aspect of the invention therefore relates to the use of the polypeptide, the nucleic acid, the vector or the cell of the invention for the preparation of a medicament for treating or preventing a disorder which can be treated or prevented by upregulating the phosphatase activity of calcineurin or by activating NFAT in eukaryotic cells.

A further aspect of the invention relates to the use of the polypeptide, the nucleic acid, the vector or the cell of the invention for the preparation of a medicament for treating or preventing a disorder which can be treated or prevented by limiting the proliferation of eukaryotic cells.

Typically, the eukaryotic cells are mammalian cells, preferably human cells, and are chosen from cancer cells, cardiomyocytes, neurones, fibroblasts, skeletal muscle cells, osteoclasts, osteoblasts or T-cells. The condition may be a pathology associated with NFAT phosphorylation state, T-cell activation state, skeletal myocyte differentiation stage, skeletal muscle dystrophy or atrophy, neurone development or bone formation. As examples of conditions in which administration of the polypeptide of the invention may be advantagous, reference may be made to Osteopetrosis (or marble bone disease), Duchenne muscular dystrophy, cancer or repair of a farcted area in the heart.

In another embodiment, the invention relates to a method for enhancing transcription of a gene in a cell, which gene is under the transcriptional control of a regulatory element, particularly a promoter, containing at least one NFAT-response element, by introducing a polypeptide according to the invention in the cell.

A further aspect of the invention therefore to the use of the polypeptide, the nucleic acid, the vector or the cell of the invention for the preparation of a medicament for treating or preventing a disorder which can be treated or prevented by the binding of the polypeptide of the invention to NS5A-TP2 in eukaryotic cells, for example for treating hepatitis C or a HCV induced liver tumors.

(B) Workflow of the screening for antiproliferative peptide aptamers. Rat XC cells are transduced with pBK1 and labelled with CMTMR. The highest percentile of fluorescent cells is then isolated by flow cytometry, and the peptide aptamer coding sequences are amplified by PCR from genomic DNA to construct sub-libraries. The sub-libraries are used in successive iterations of this process.

Figure 2:
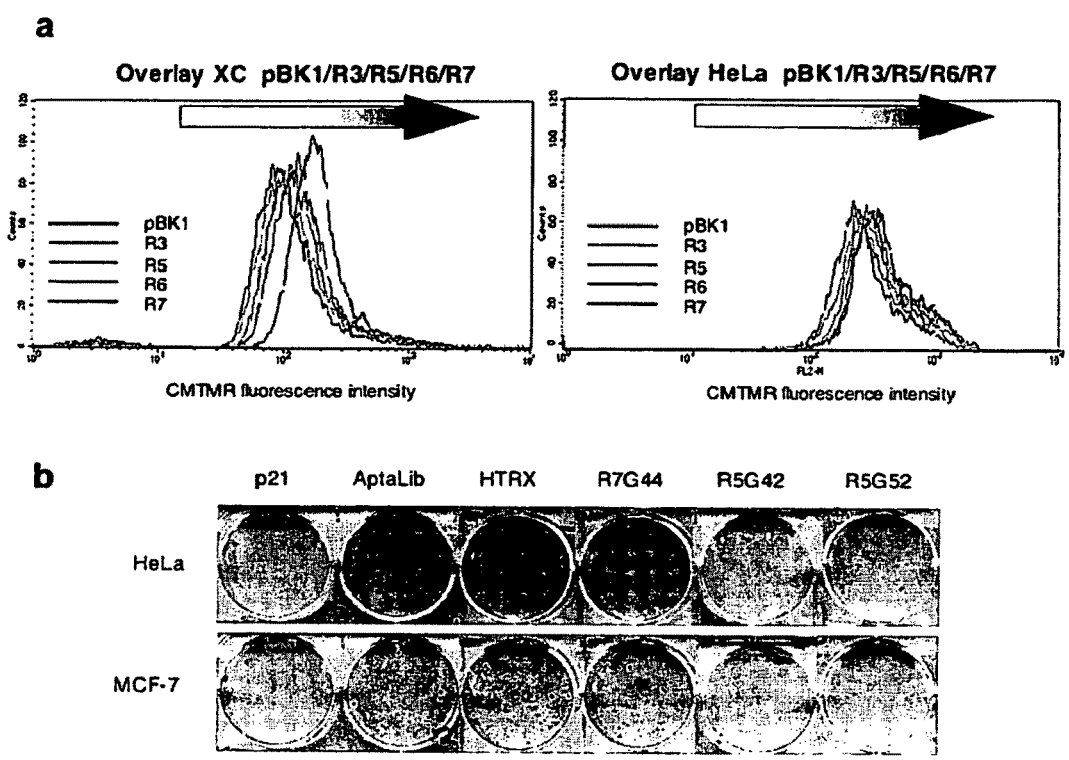

FIG. 2. Antiproliferative Effect of Peptide Aptamers (A) Progressive enrichment of peptide aptamer sublibraries in antiproliferative peptide aptamers through screening iterations. XC or Hela cells were transduced with pBK1 or different R"n" sub-libraries obtained after n screening iterations, and were labelled with CMTMR. The mean fluorescent intensity increases with the number of screening iterations, indicating a progressive enrichment in peptide aptamers exerting an antiproliferative effect.

(B) Colony formation assays. Hela or MCF-7 cells were transfected with plasmids directing the stable expression of the Cdk inhibitor p21, a library of peptide aptamers from pBK1 (AptaLib), Human thioredoxin (HTRX), and peptide aptamers R7G44, R5G42, R5G52. The cells were cultured for two weeks and the colonies were stained with crystal violet.

Figure 3:
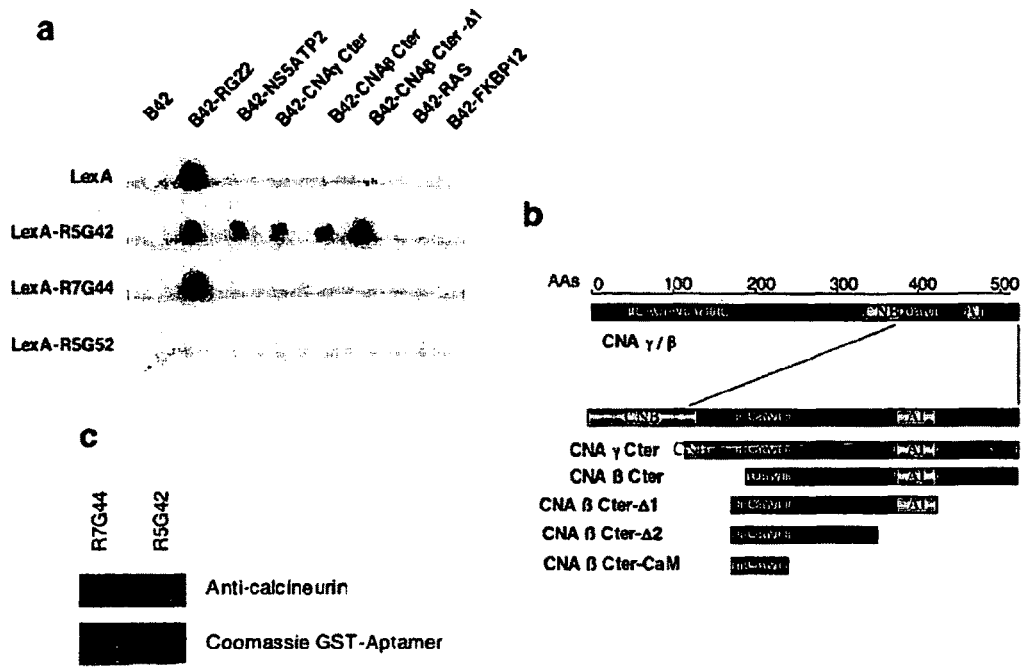

FIG. 3. Interaction Between Peptide Aptamer R5G42 and Calcineurin A (A) Yeast two-hybrid mating assay. TB50α yeast were co-transformed with pSH18-34T (bearing a lacZ reporter gene) and plasmids directing the expression of LexA alone or in fusion with peptide aptamers R5G42, R7G44 or R5G52. MB210a yeast were transformed with the selected cDNA library plasmids directing the expression of CNAβ, CNAγ, and NS5ATP2 truncated proteins. To obtain negative controls, MB210a yeast were also transformed with the empty prey plasmid (pJG4-5) and with pJG4-5 directing the expression of Ras and FKBP12 prey proteins. To obtain a positive control, MB210a yeast were transformed with pJG4-5 directing the expression of RG22 peptide aptamer prey fusion protein that interacts with LexA in the context of most LexA fusion proteins.

(B) Schematic representation of the CNA clones selected through the yeast two-hybrid screening and of the truncations performed on CNAβ.

CNA beta C ter-delta 1: amino acids 378 to 500
CNA beta C ter-delta 2: amino acids 378 to 456
CNA beta C ter-CaM: amino acids 378 to 423

(C) Affinity capture assay. Comparable amounts of GST-R7G44 or GST-R5G42 recombinant fusion proteins were coupled to glutathione-sepharose beads. Purified calcineurin was added onto the beads and the captured molecules were revealed by a western blot experiment using an anti-calcineurin antibody.

Figure 4:
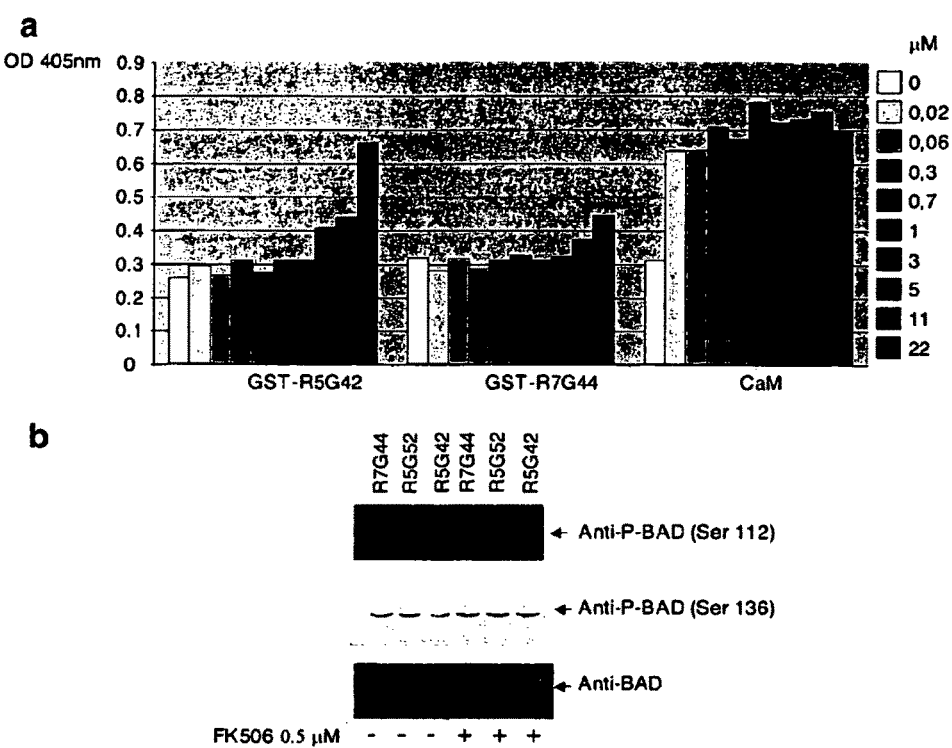

FIG. 4. Stimulation of Calcineurin Activity by Peptide Aptamer R5G42

(A) In vitro calcineurin phosphatase assay. Dephosphorylation of the model substrate pNPP by purified calcineurin was measured in presence of various amounts of purified calmodulin (CaM), GST-R5G42 or GST-R7G44 fusion proteins.

(B) Monitoring of BAD phosphorylation in cultured cells. Hela-Tet cells were transfected with plasmids directing the transient expression of BAD, CNAβ, CNB and peptide aptamers R5G42, R5G52 or R7G44. Transfected cells were treated or not with 500 nM FK506. The expression level of BAD and the phosphorylation of serine 112 and 136 residues were monitored by western blot experiments using specific antibodies.

FIG. 5. Human Calcineurin A Isoforms (A) amino acid sequence of calcineurin A alpha isoform (SEQ ID 16)

(B) amino acid sequence of calcineurin A beta isoform (SEQ ID 17)

(C) amino acid sequence of calcineurin A gamma isoform (SEQ ID 18)

FIG. 6. NS5A-TP2

Amino acid sequence of NS5A-TP2 (SEQ ID 15)

FIG. 7. Human Thioredoxin

Amino acid sequence of human thioredoxin (SEQ ID 19)

FIG. 8. R5G42 and R5G42 Mutants

Amino acid sequences of R5G42 (SEQ ID 22) and of the R5G42 C2, C3, C4, C5, C7, C8, C12, N9 and N12 mutants (SEQ ID 23-29 and 33-34).

Figure 9:
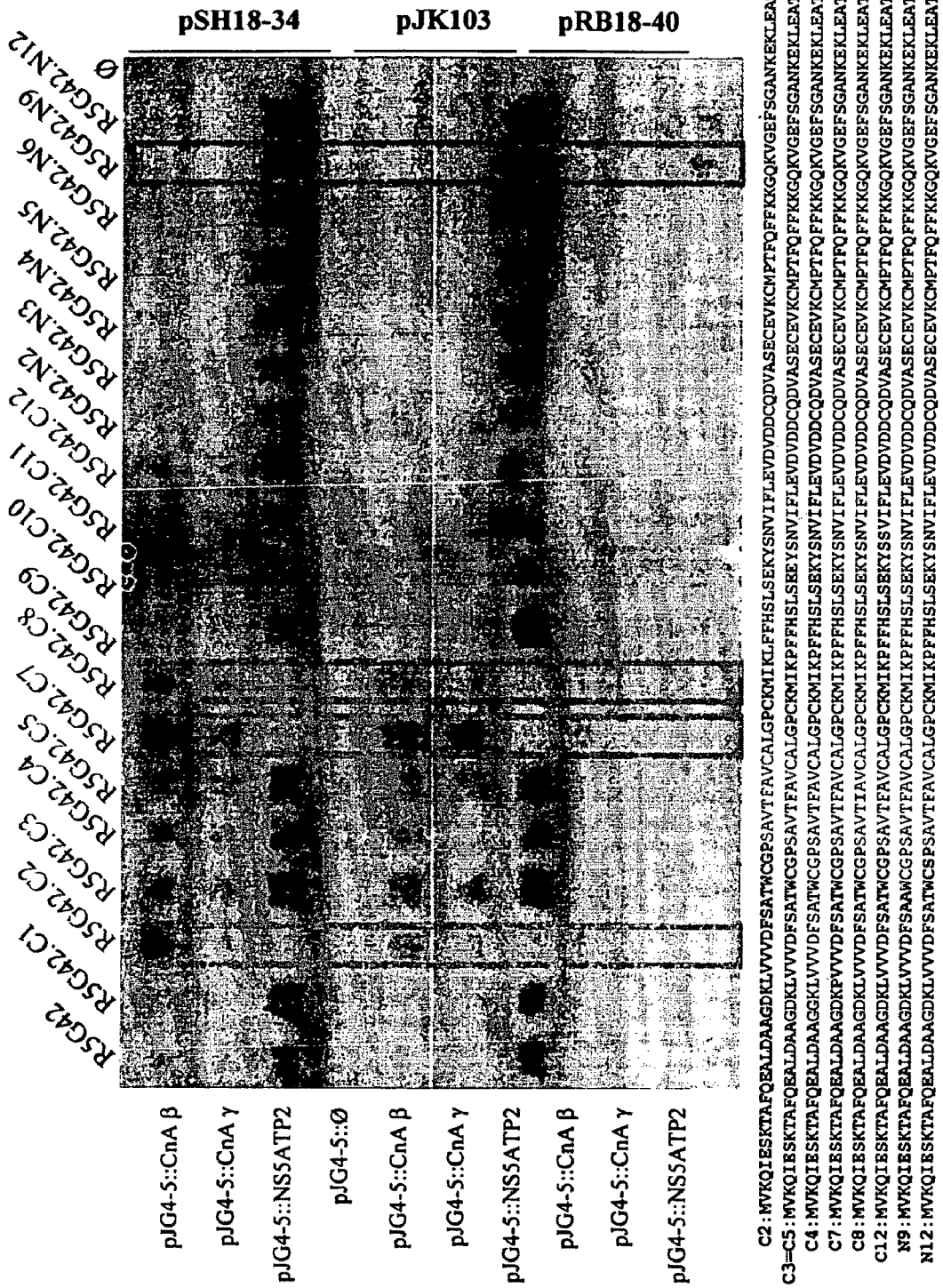

FIG. 9. Interaction Matrix Between R5G42 Mutants and CNA Beta, CNA Gamma and NS5A-TP2

The capacity of R5G42 mutants having a one amino acid change as compared to R5G42 to bind CNA beta and gamma C-Terminal fragments (FIG. 3b) and NS5A-TP2 was tested in yeast two-hybrid assays. CNA beta and gamma C-Terminal fragments and NS5A-TP2 were cloned in three different vectors (pSH18-34, pJK103 and pRB18-40). These three plasmids differ from each other in the level of sensitivity of their promoter, pSH18-34 having the highest sensitivity and pRB18-40 having the lowest.

R5G42 mutants C2, C7 and C8 were shown to interact with the CNA beta and gamma C-terminal fragments but not with NS5A-TP2, and R5G42 mutant N9 (SEQ ID 33) was shown to interact with NS5A-TP2 but not with the CNA beta and gamma C-terminal fragments.

Figure 10:
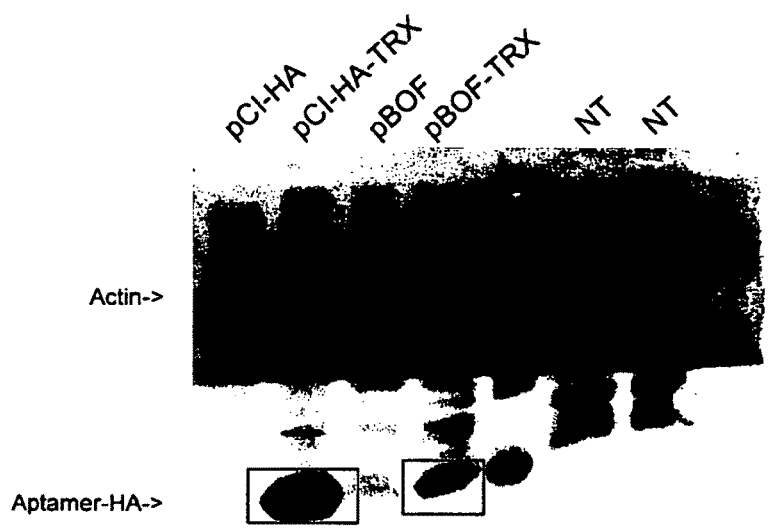

FIG. 10. Expression of Human TRX in HeLa Cells Transfected with pCI-HA or pBof Plasmids From equivalent total protein amounts (revealed by the intensity of the anti-Actin labelling), HA labelled Trx is only detected with plasmids pCI-HA/Trx and pBof/Trx. However, in the context of pBof, the expression lever is lower.

Figure 11:

FIG. 11. Expression of Aptamers According to the Invention in HeLa Cells.

HeLa cells were transfected with pCI-HA plasmids containing either an empty vector, Trx, R5G42, C2, C7, C8, N9 and R5G52. Expression in the cells of Trx, R5G42, C2, C7, C8 and N9 was confirmed by a Western Blot.

Figure 12B:
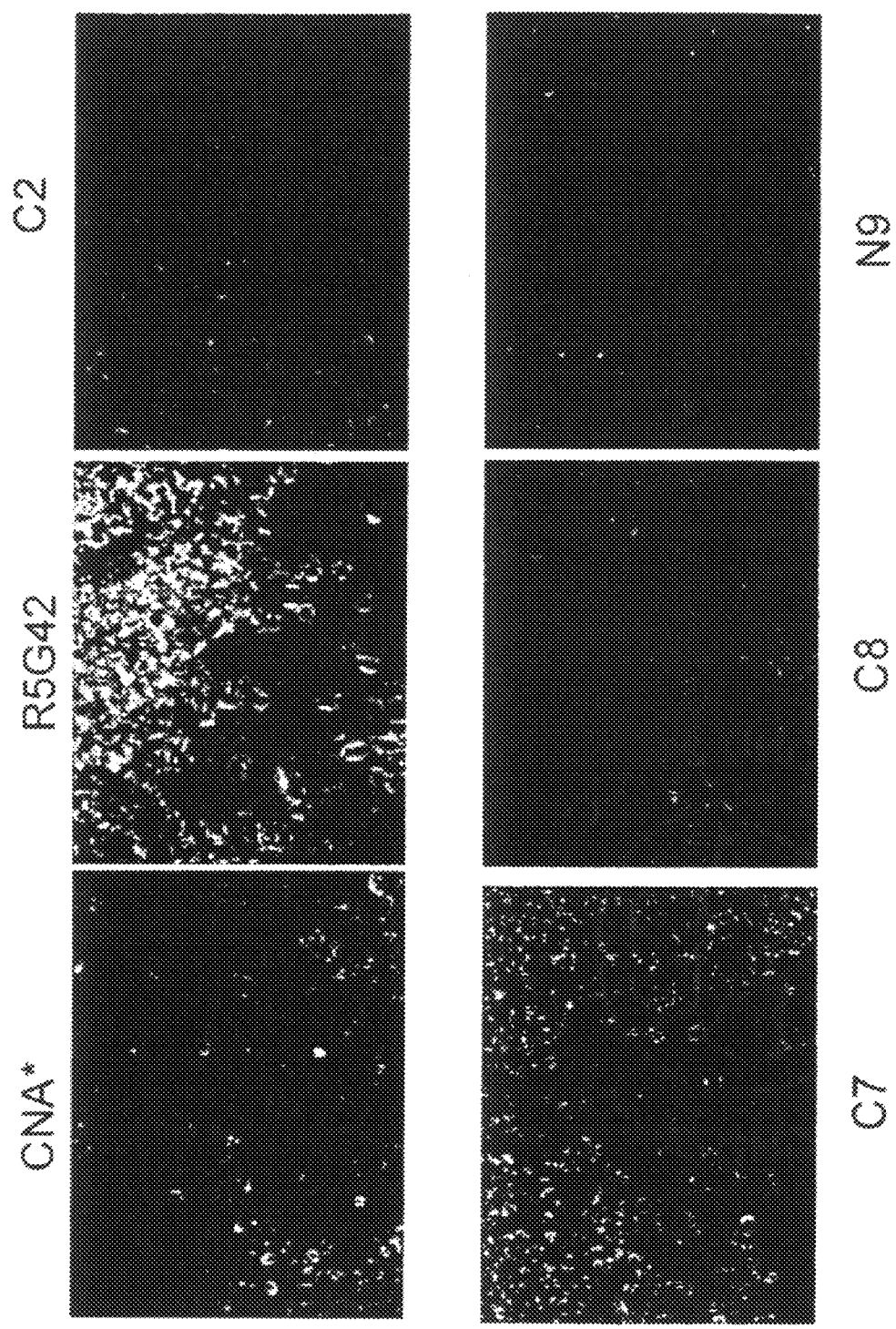

FIG. 12. Effect of Peptide Aptamers According to the Invention on Osteoclast Differentiation Trx, CNA* and Peptide aptamers R5G42, C2, C7, C8 and N9 were transfected into RAW1 cells and left for four days in absence of the normal differentiation factor RANKL. CNA* is activated calcineurin A which elicits a robust differentiation response. The results show that differentiation is induced by the aptamers R5G42 and C7.

A. Transfection of RAW1 cells with an empty vector and addition of RANKL two days after transfection (positive control), and transfection with a vector containing TRX (negative control). B. Transfection OF RAW1 cells with vectors containing CNA* (positive control for differentiation activation) and the peptide aptamers R5G42, C2, C7, C8 and N9

Figure 13:
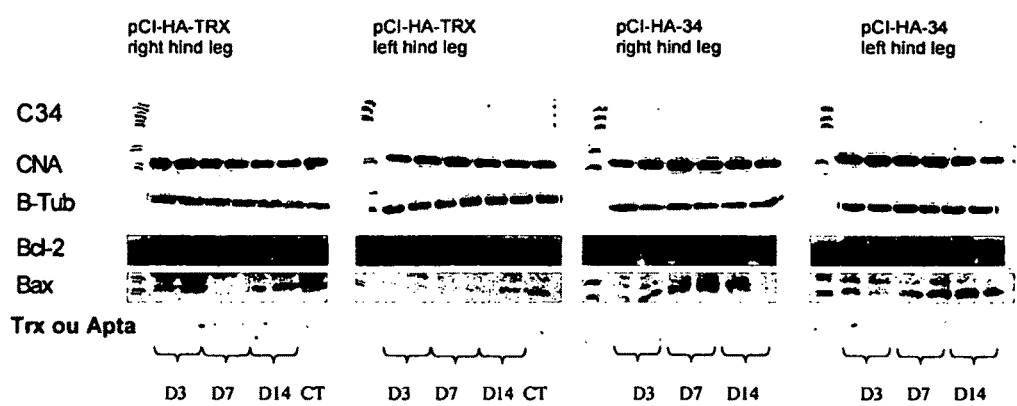

FIG. 13. Expression of Proteins in Mice Muscles After Electroporation and Denervation Mice hind legs received an injection followed by electroporation of plasmids containing Thioredoxin (TRX) or a control aptamer (34). Their left hind legs were then denerved. Control mice (CT) received only an NaCl injection. Total proteins were extracted for an analysis of the expression of certain key proteins among which TRX, the aptamer 34 and its target (C34), Calcineurine A (CNA), beta-Tubuline (B-Tub), Bcl2 and Bax. It is to be noted that the fibers having incorporated the vectors (pCI-HA-TRX, pCI-HA-34) only represent a fraction of the muscle analysed.

Figure 14:
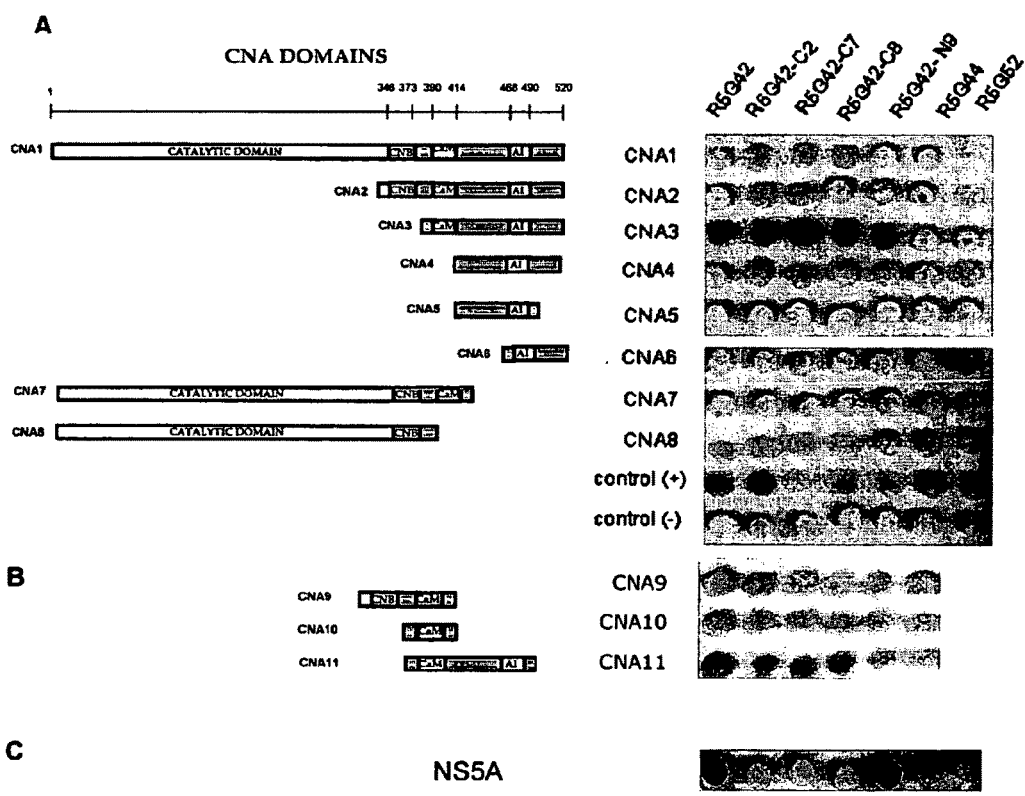

FIG. 14. Specificity of Aptamers According to the Invention for CNA and NS5A-TP2

Interaction matrix between peptide aptamers R5G42, C2, C7, C8, N9, R5G44 and R5G52 with CNA constructs CNA1-CNA8 (A) CNA9-11 (B) and NS5A-TP2 (C). An interaction phenotype between CNA3/CNA 11, which both contain the Calmodulin binding domain (CaM) and the auto-inhibitory domain (AI) but not the CNB binding domain (CNB) and the aptamers R5G42, C2, C7, C8 and N9 is observed in a two-hybrid assay. R5G44 and R5G52 aptamers recognize neither the CNA fragments, nor NS5A-TP2. Only aptamers R5G42 and N9 recognize NS5A-TP2.

Figure 15:
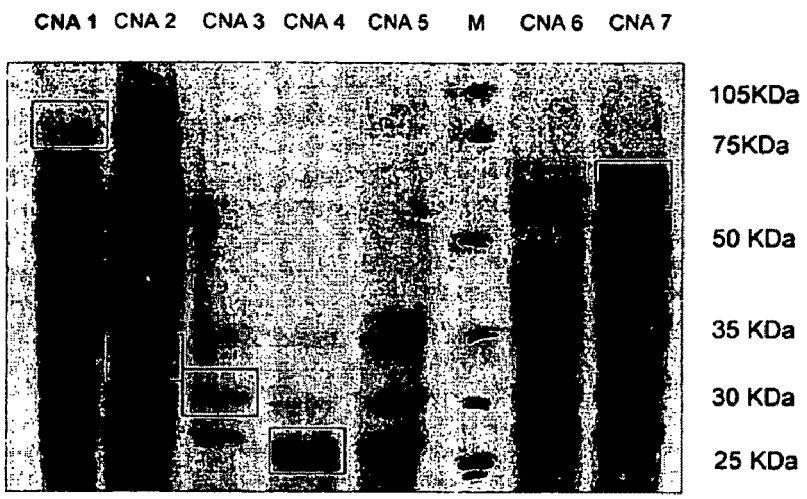

CNB: CNB binding domain; CaM: Calmodulin binding domain; AI: auto-inhibitory domain FIG. 15. Detection of the Expression of CNA Constructs in Yeast In order to check the expression of the CNA constructs CNA1 to CNA7 in the two-hybrid assay, a cellular lysate was performed followed by Western Blot detection. The molecular weights of the different constructs are represented in the squares. For CNA5 and CNA6, no bands are detected which is probably due to their small size (about 19 kDa)

Figure 16:
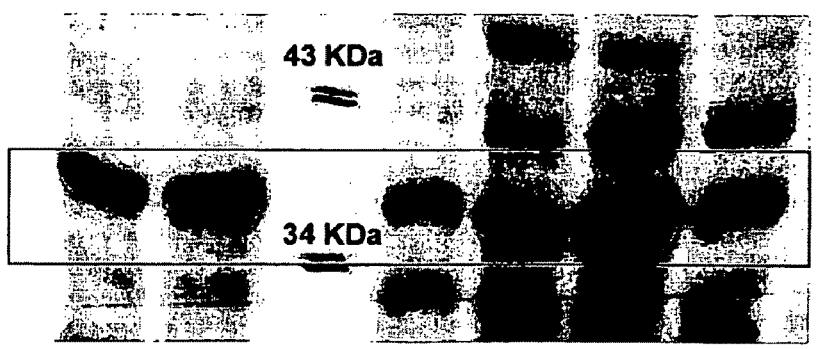

FIG. 16. Detection of the Expression of Aptamers According to the Invention in Yeast The lysis of the yeasts was performed on colonies obtained after the mating of mat a and mat alpha strains and the determining of the two-hybrid phenotype. Aptamers R5G42, C2, C7, C8, N9 and R5G52 are in the LexA-pGILDA vector. Their expression was detected unsing an antibody which recognize LexA.

FIG. 17. Amino Acid Sequences of CNA1-CNA11 (SEQ ID 35-45)

Figure 18:
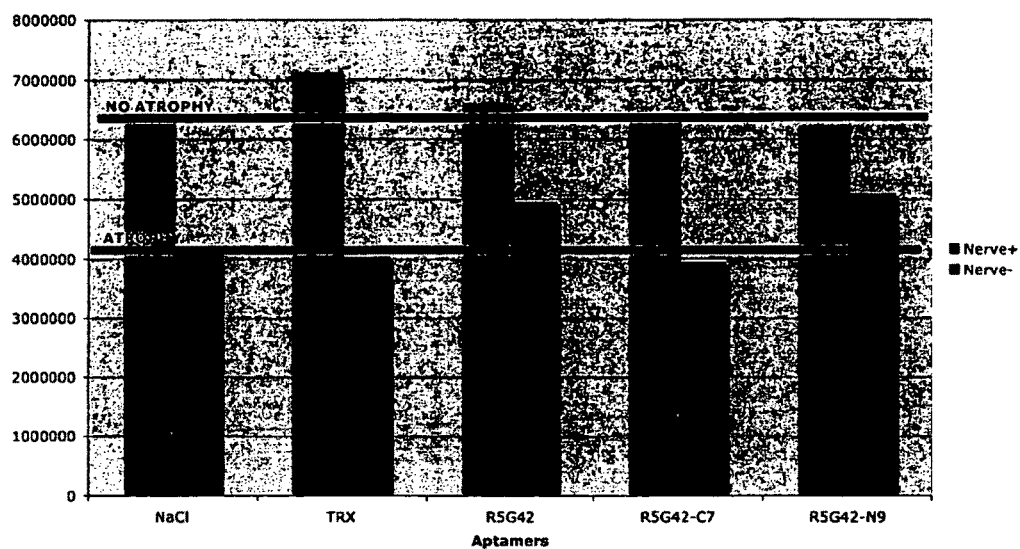
Figure 18:
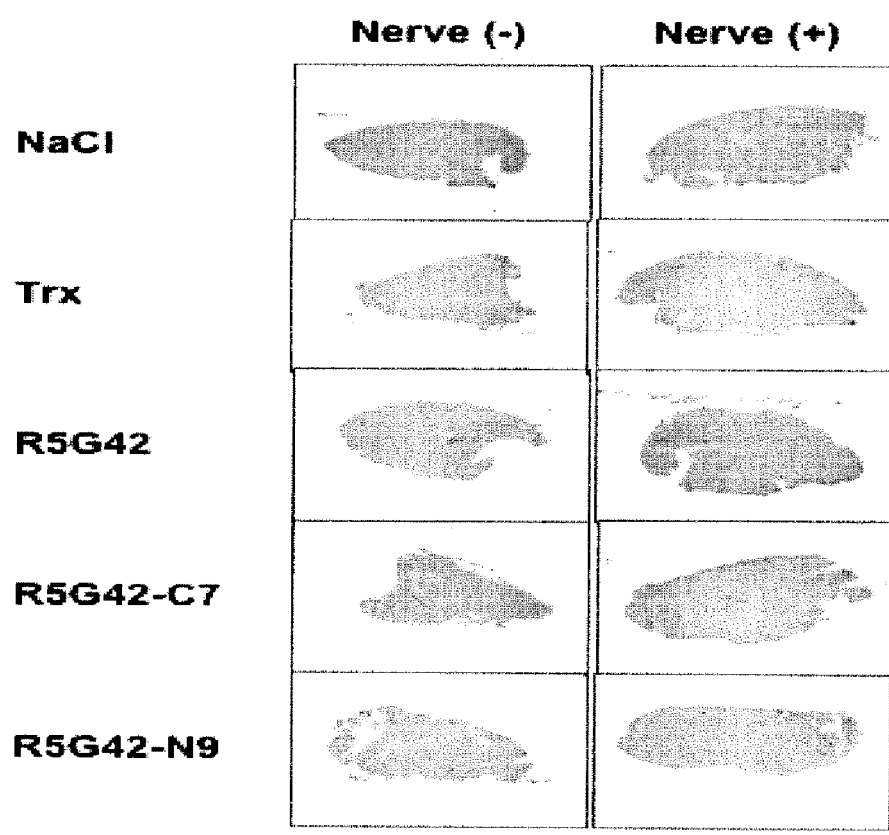

FIG. 18. Measure of the Tibialis Anterior Area 14 Days Post-Denervation

Vectors containing TRX, the R5G42, C7 or N9 aptamers or NaCl (control) were electroporated in mice hind legs (day 1) and an unilateral abolition of the motor innervation of the tibia muscles of the left hind leg was performed (day 3). After euthanasia of the mice (day 17) the tibialis anterior area was measured.

Without denervation, the muscle area is relatively stable from one experiment to another (6.532.412+/−351.070, or 5.3% of variation). With denervation a reduced atrophy effect of about 27% and 48% is observed with aptamers R5G42 and N9 as compared to the atrophy effect obtained using the NaCl control (See FIGS. 19-20). The 100% of atrophy effect was evaluated using the data obtained with the NaCl control.

A-B. Measure of the the tibialis anterior area with (left hind leg) or without (rigth hind leg) denervation—C. Section of the tibialis anterior area 14 days post-denervation

EXAMPLES

The inventors set out to identify and isolate combinatorial protein reagents capable of inhibiting tumor cell proliferation.

A peptide aptamer library was built in a lentiviral expression system to isolate aptamers that inhibit cell proliferation in vitro. Using one of the isolated aptamers (R5G42), as a bait protein, a yeast two-hybrid screening of cDNA libraries was performed and calcineurin A (CNA) was identified as a target protein candidate. R5G42 binds CNA in vitro and stimulates its phosphatase activity. When expressed transiently in human cells, R5G42 induces the dephosphorylation of Bad.

The use of this ligand is therefore likely to help elucidate the still elusive structural mechanisms of activation and inhibition of calcineurin.

In the experiments reported in the following examples, the inventors have constructed a peptide aptamer library in a simian immunodeficiency virus (SIV)-derived gene expression system. They have performed an iterative genetic screening to isolate peptide aptamers that inhibit tumor cell proliferation. They have identified the catalytic subunit of the calcium-activated protein phosphatase calcineurin as a target of one of the isolated aptamers. They have shown that this aptamer upregulates the phosphatase activity of calcineurin in vitro and in cultured cells. Their work has identified an antiproliferative molecule that binds and stimulates calcineurin through a seemingly original mechanism.

The inventors have shown that an antiproliferative peptide aptamer (R5G42) binds CNA and activates its phosphatase activity in vitro. Consistent with the in vitro results, the transient expression of R5G42 in human cells induces the dephosphorylation of Bad on Serine 136, which is totally reversed by FK506. The expression of R5G52, another antiproliferative peptide aptamer, does not affect Bad phosphorylation levels. Altogether, these results indicate that Bad dephosphorylation is specifically caused by the activation of CNA by R5G42, as opposed to being an indirect consequence of an antiproliferative activity.

The antiproliferative effect of R5G42 could stem from a calcineurin-mediated induction of apoptosis, which would only occur upon prolonged expression of the peptide aptamer. Details of the Materials and Methods Employed in the Following Examples 1 to 7 are Provided in Example 7

Example 1

Peptide Aptamer Libraries and Screening Strategy

Figure 1:
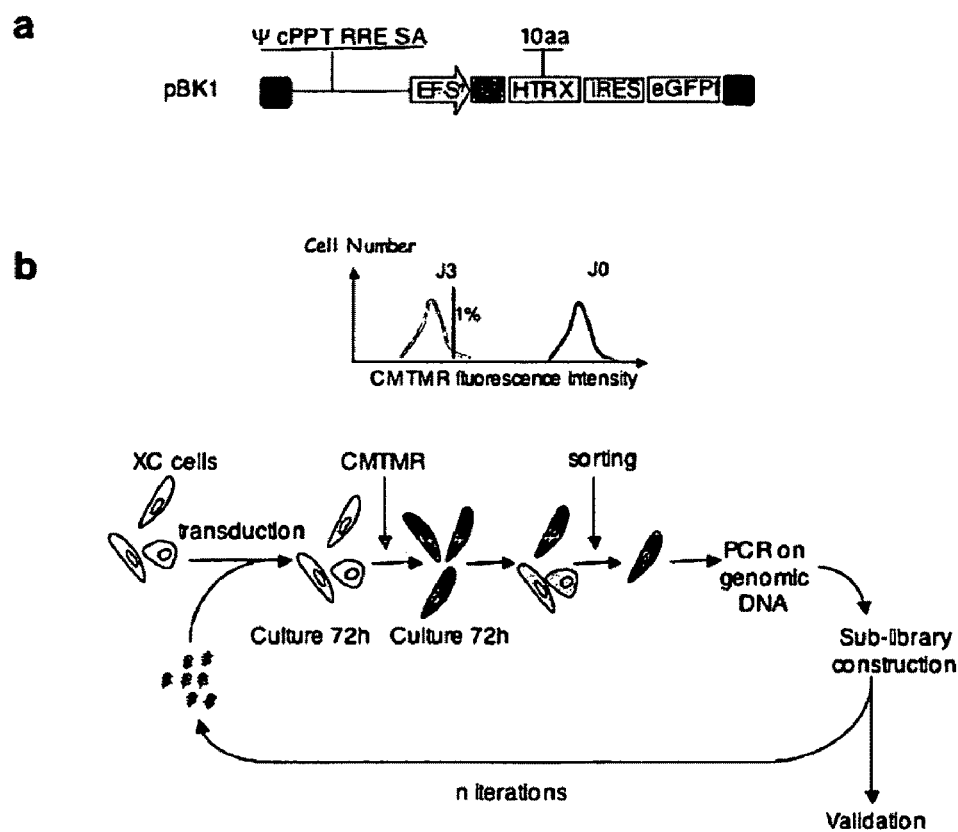
FIG. 1. Design of the Peptide Aptamer Library and of the Antiproliferative Screening (A) Schematic representation of the pBK1 peptide aptamer library. This SIV-derived expression system directs the expression of two cistrons coding for a EGFPf transduction marker and HA-tagged peptide aptamers consisting of a 10 aminoacid variable region inserted within the active site of human thioredoxin.

To construct their peptide aptamer libraries, the inventors used a SIV-derived lentiviral expression vector directing the constitutive expression of bicistrons (transgenes and a GFP marker) under the control of an EF1α promoter (see Example 6 for experimental procedures). They first built 12 low-complexity peptide aptamer libraries, combining two scaffolds (human thioredoxin or a E. coli thioredoxin, whose coding sequence harbors codons optimized for expression in mammalian cells), two epitope tags (HA or 6His) and three variable region lengths (16, 10 or 7 amino acids). They performed pilot experiments to determine which library yielded the highest expression level of peptide aptamers upon transduction of XC cells with viral particles. They observed that the best combination was the HA-tagged, human thioredoxin displaying a random peptide loop of 10 amino acids and they constructed accordingly pBK1, a high-complexity peptide aptamer library (see FIG. 1A).

To isolate library members that inhibit tumor cell proliferation, the inventors made use of the fluorescent vital dye CMTMR (5-(and-6)-(((4-chloromethyl)benzoyl)amino)tetramethylrhodamine), which cells incorporate and dilute, as they proceed through division cycles. Those cells that do not divide maintain a high fluorescence level and can thus be sorted by flow cytometry. Because of a significant background of cells that do not grow or proliferate more slowly independent of the expression of peptide aptamers, multiple screening rounds were necessary to isolate peptide aptamers that exert an antiproliferative effect. The inventors thus constructed a peptide aptamer sub-library from the highest percentile of CMTMR-positive cells obtained after each screening iteration and they submitted each sub-library to a subsequent screening round (see FIG. 1B).

Example 2

Isolation of Antiproliferative Peptide Aptamers

The inventors used rat XC cells, derived from a RSV-induced sarcoma, which enabled them to use viral particles harboring a murine ecotropic envelope. They performed 7 screening iterations before isolating and characterizing individual peptide aptamers. They determined the antiproliferative activity of the sub-libraries both in XC cells and in human HeLa cells. As shown in FIG. 2A, the mean fluorescence intensity of both cell lines increases gradually with the number of screening iterations, thereby indicating a progressive enrichment of antiproliferative peptide aptamers within the sub-libraries.

The inventors picked and sequenced 100 clones from the R5 and R7 sub-libraries, obtained from the fifth and seventh screening iteration, respectively. More than 40% of the peptide aptamers isolated after the seventh screening iteration corresponded to a single library member, named R5G42. The occurrence of this aptamer was already significant after the fifth iteration but was not detectable after the fourth iteration. Three other peptide aptamers that showed a lower occurrence were also isolated (R7G11 (SEQ ID 30), R7G44 (SEQ ID 31) and R5G52 (SEQ ID 32)) (see Table 1).

The inventors wished to establish the antiproliferative activity of these peptide aptamers using alternative cellular models and a non-retroviral vector to express individually each aptamer. They cloned the aptamer coding genes into a vector bearing a hygromycin selection marker. They also subcloned the pBK1 library into this vector, to create "AptaLib". They continuously expressed the aptamers, the empty thioredoxin scaffold or AptaLib in Hela and MCF-7 cells for 2 weeks and they stained the cells that grew. Aptamers R5G42 and R5G52 significantly inhibited the proliferation of both cell lines, as compared to AptaLib and human thioredoxin. Aptamer R7G44, similarly to other aptamers (not shown), did not exert any antiproliferative effect (see FIG. 2B). These aptamers may originate from the remaining background of slowly proliferating cells during the seventh screening iteration, independently of the expressed aptamers. Surprisingly, aptamer R7G11 did not inhibit cell proliferation in this assay (not shown), despite showing a high occurrence in the seventh sub-library (Table 1). This could be due to the fact that the CMTMR assay is more sensitive in detecting modest antiproliferative effects than the colony formation assay or that some peptide aptamers somehow enhance the CMTMR labeling of their host cells. From all these results, it was decided to focus on peptide aptamer R5G42 and to identify its target protein.

Example 3

Identification of Calcineurin A and NS5A-TP2 as Target Proteins

The inventors performed two yeast two-hybrid screening experiments against a LexA-R5G42 bait protein, using a human testis and a human fœtal brain cDNA library. They obtained 29 and 42 reconfirmed clones, respectively. They disregarded those clones that either showed a barely detectable two-hybrid interaction phenotype, or that cross-interacted with control aptamers, or that corresponded to hypothetical proteins (Table 2). The inventors thus retained two candidates. The highest occurring clone, from both libraries, corresponded to the NS5A-TP2 protein, recently discovered through a systematic search for genes that are transactivated by the non-structural NS5A protein from hepatitis C virus (22). No biological knowledge is currently available for this protein. The other remaining target candidate was calcineurin A (CNA), for which two different isoforms (beta and gamma) were selected from the testes library (see FIG. 3A).

To confirm the interaction between R5G42 and CNA, the inventors performed an in vitro binding assay between recombinant purified GST-aptamer fusion proteins, coupled to a glutathione-sepharose matrix, and purified CNA. The GST-R5G42 solid phase readily captured CNA, as opposed to a GST-R7G44 control (see FIG. 3C).

Example 4

Mapping of the R5G42 Binding Site on CNA and Mutations of R5G42

Mapping of the R5G42 Binding Site on CNA
The inventors set out to map the R5G42 binding site on CNA. The CNA interacting clones selected in the yeast two-hybrid experiments corresponded to the carboxy-terminal regions of the beta and gamma isoforms, encompassing the calmodulin-binding domain and the auto-inhibitory domain (see FIG. 3B). Among the 3 truncations constructed from the CNAβ selected clone (see FIG. 3B), only CNAβΔ1 retained its yeast two-hybrid interaction phenotype with R5G42 (see FIG. 3A and data not shown). These results indicate that the R5G42 binding site on CNA lies between the amino-terminus of the calmodulin-binding domain and the carboxy-terminus of the auto-inhibitory domain, and is not circumscribed to the CaM binding domain. This yeast two-hybrid mating assay also supports the specificity of interaction between R5G42 and CNA, as R5G42 did not show an interaction phenotype with two unrelated bait proteins (RAS, FKBP12) and as R7G44 and R5G52 did not show an interaction phenotype with CNA. R5G52, however, did not show an interaction phenotype with peptide aptamer RG22, which interacts with LexA in the context of most (but not all) LexA fusion proteins. The LexA-R5G52 bait protein may thus not be properly expressed and/or folded in this yeast two-hybrid setting.

Mutations of the R5G42 Amino Sequence
The inventors explored the ability of R5G42 mutants having a one amino acid change as compared to R5G42, to bind to CNA beta and gamma C-Terminal fragments (FIG. 3b) and to NS5A-TP2. To this end, they proceeded to yeast-two hybrid assays as in example 3. CNA beta and gamma C-Terminal fragments (FIG. 3b) and NS5A-TP2 were cloned in three different plasmids (pSH18-34, pJK103 and pRB18-40), which differed from each other in the level of sensitivity of their promoter to the bait/prey complex formation, pSH18-34 having the highest sensitivity and pRB18-40 having the lowest.

R5G42 mutants C2 (SEQ ID 23), C7 (SEQ ID 27) and C8 (SEQ ID 28) were shown to interact with the CNA beta and gamma C-terminal fragments but not with NS5A-TP2, and R5G42 mutant N9 (SEQ ID 33) (see FIG. 8) was shown to interact with NS5A-TP2 but not with the CNA beta and gamma C-terminal fragments (FIG. 9). The inventors thereby showed that point mutation in the R5G42 amino acid sequence allowed to identify mutants sequence with an increased selectivity for each of the targets identified for R5G42.

Binding of R5G42 and R5G42 Mutants to Subsequences of CNA and to NS5A-TP2
The inventors proceeded to further yeast two-hybrid binding assays between peptide aptamers R5G42 (SEQ ID 22), C2 (SEQ ID 23), C7 (SEQ ID 27), C8 (SEQ ID 28), N9 (SEQ ID 33), R5G44 and R5G52 with CNA constructs CNA1-CNA8 (FIG. 14A), CNA9-CNA11 (FIG. 14B) and NS5A-TP2 (SEQ ID 15) (FIG. 14C). The sequences of CNA1-CNA11 (SEQ ID 35-45) are shown in FIG. 17. The sensitivity of this yeast two-hybrid assay was higher than in the experiment reported above.

An interaction phenotype between each of CNA3 and CNA 11, which both contain the Calmodulin binding domain (CaM) and the auto-inhibitory domain (AI) but not the CNB binding domain (CNB) and the aptamers R5G42, C2, C7, C8 and N9 was observed. R5G44 and R5G52 aptamers (negative controls) recognized neither the CNA fragments, nor NS5A-TP2. The only aptamers which recognized NS5A-TP2 were R5G42 and N9 (FIG. 14).

The fact that CNA1 and CNA2 which both contain the Calmodulin binding domain (CaM) and the auto-inhibitory domain (AI) as well as the CNB domain did not interact with the aptamers of the invention appears to be due to an artefact of the yeast two hybrid protocol. Indeed, the inventors dearly showed in the Bad dephosphorylation assay in mammalian cells commented in example 5, that endogenous CNA was activated on transfecting R5G42 into the cells.

Example 5

Modulation of Calcineurin Activity In Vitro and in Mammalian Cells

Activation of CNA Phosphatase Activity In Vitro
The inventors next explored the ability of R5G42 to modulate the enzymatic activity of its target protein. To this end, they first performed an in vitro phosphatase assay using purified CNA and para-nitrophenylphosphate (pNPP) as a substrate. As shown in FIG. 4A, the addition of purified calmodulin (CaM) is required to activate CNA. The addition of recombinant purified GST-R5G42 did not result in an inhibition or an exacerbation of CaM-activated CNA phosphatase activity (not shown). However, the addition of high concentrations of GST-R5G42 activated CNA phosphatase activity in absence of CaM, to a level comparable to that observed using CaM. The addition of equal amounts of the control aptamer R7G44 did not produce a significant effect. This experiment indicates that R5G42, like CaM, binds and activates CNA phosphatase activity in vitro.

Dephosphorylation of Bad in HeLa Cells
The inventors set out to confirm this finding in human cells. Bad is a key pro-apoptotic protein whose activity is tightly regulated by its phosphorylation status, itself controlled by the balanced activity of several protein kinases and calcineurin. Therefore, the phosphatase activity of calcineurin in cells can be monitored by examining Bad phosphorylation. HeLa cells were transfected with plasmids directing the expression of Bad, CNAβ, CNB and either R5G42, R5G52 or R7G44. The inventors observed that expression of R5G42 decreased the phosphorylation of Bad on serine 136, without affecting the phosphorylation on serine 112 (see FIG. 4B). To demonstrate that this effect was caused by an upregulation of calcineurin activity, they performed the same experiments in presence of FK506, a well-known inhibitor of calcineurin. The R5G42-induced dephosphorylation of Bad on serine 136 was no longer observed in presence of FK506 (see FIG. 4B).

Effect of Aptamers According to the Invention on Osteoclast Differentiation
Osteoclasts are bone-resorbing, multinucleated cells that differentiate from monocyte precursors. The differentiation of osteoclasts is dependant on a tumor necrosis factor (TNF) family cytokine, receptor activator of nuclear factor (NF)-κB ligand (RANKL), as well as macrophage colony-stimulating factor (M-CSF) (30).

Recent studies have suggested that the nuclear factor of activated T-cells (NFATc1) is a master switch for osteoclastogenesis in reponse to RANK receptor activation (31).

The necessary and sufficient role of NFATc1 in osteoclastogenesis was suggested by the in vitro observation that NFATc1$^{-/-}$ embryonic stem cells do not differentiate into osteoclasts (32).

The activation of NFAT c1 as well as of NFAT c2/c3/c4 is mediated by the calcium/calmodulin dependant phosphatase, calcineurin A (CNA).

The inventors assessed the ability of some CNA-specific peptide aptamers to promote osteoclast differentiation via the activation of CNA. Raw1 cells (osteoclasts precursors) were transfected with the following plasmids: pCI-HA-Trx (negative control), pCI-HA CNA* (positive control for differentiation activation), pCI-HA R5G42, pCI-HA R5G42-C2, pCI-HA R5G42-C7, pCI-HA R5G42-C8 and pCI-HA R5G42-N9 (this last point mutant shows a dramatic reduction of the two hybrid interaction phenotype against CNA compared to R5G42). The differentiation state was then observed 4 days post-transfection. As expected, cells in control conditions (with RANKL) were differentiated into osteoclasts.

Some cells with the osteoclast phenotype can be observed with CNA*, R5G42, and R5G42-C7 (see FIG. 12), indicating that these proteins are able to initiate and fulfill the differentiation process. Nevertheless with the negative control R5G42-N9 and the C2 and C8 mutants, some cells with several nuclei can be observed but no osteoclasts fully differentiated were detectable in this experimental period.

Thus, the aptamers R5G42 and R5G42-C7 exert an effect on CNA sufficient to permit the differentiation of monocyte-derived cells into osteoclasts in the absence of RANKL.

Example 6

In Vivo Denervation Assay in Mice Tibia Muscles

Mice hind legs first received an injection of plasmids containing Thioredoxin (TRX), a control aptamer (34) or only NaCl, followed by electroporation. Their left hind legs were then denerved. After euthanasia, total proteins were extracted, and the expression of certain key proteins among which TRX, the aptamer 34 and its target (C34), Calcineurin A (CNA), beta-Tubuline (B-Tub), Bcl2 and Bax was checked. The level of CNA expression in muscle was high and TRX and the control aptamer 34 cloned in the pCI-HA vector were detected (see FIG. 13).

Another group of mice hind legs were electroporated after the injection of vectors containing TRX, the R5G42, C7 or N9 aptamers or with NaCl (control) at day 1. A unilateral abolition of the motor innervation of the tibia muscles of the left hind leg was performed at day 3 in order to induce a muscular atrophy. The mice were then euthanised at day 17, i.e. 14 days after sciatic denervation of the left hind leg. The measure of the tibialis anterior area 14 days post-denervation showed that without denervation (right hind leg), the muscle area is relatively stable from a one experiment to another (6.532.412+/−351.070, or 5.3% of variation). With denervation a reduced atrophy effect of about 27% and 48% is observed with aptamers R5G42 and N9 as compared to the atrophy effect obtained using the NaCl control (FIG. 18).

Example 7

Materials and Methods

The following section describes the materials and methods used in the above-described examples.

Cell Culture

All mammalian cells were maintained in a 5% $CO_2$ atmosphere at 37° C. in Dulbecco's Modified Eagle's Medium (Invitrogen-Gibco) supplemented with 10% v/v fetal calf serum and 100 microg/ml penicillin-streptomycin.

Construction of Lentiviral Vectors

All the lentivectors were derived from pR4SA-EFS-GFP-W (19). This vector first was digested with Hind III, thus eliminating EGFP, WPRE and EcoRI sites, to create pVRV1. The remaining EcoRI site upstream of the CMV promoter was blunted and the vector was religated to create pVRV2. pVRV2 was digested with BamHI and HindIII and the following hybridized oligodeoxynucleotides:

```
                                                 (SEQ ID 1)
5'-GATCGCTAAGCGAATTCCTCGAGGCGCGCGTCGACCAGGATCC-3' and (SEQ ID 2)
5'-AGCTTGGATCCTGGTCGACGCGCGCCTCGAGGAATTCGCTTAGC-3'
``` were ligated to create pVRV3, that bears a multiple cloning sequence. pVRV4 was constructed by inserting an IRES-EGFPf (farnesylated enhanced GFP) coding sequence in pVRV3. This was done by a multiplex ligation between SalI/BamHI-cut pVRV3, a SalI/NcoI-cut EMCV IRES cassette (from pIRES2-EGFP, Clontech) and a NcoI/BamHI-cut EGFP-f coding sequence (from pEGFP-F, Takara Bio). A HA-tagged HTRX fragment from pJMX-HTRX (Abed et al, in preparation) was then PCR amplified using the oligonucleotides

```
5'-GCGGCTAAGCCATGTACCCTTATGATGTGCCAG-3'  (SEQ ID 3)

and

5'-GGAGACTTGACCAAACCTCTG-3'              (SEQ ID 4)
``` and this fragment was ligated into BlpI/XhoI-cut pVRV4. The resulting plasmid, pVRV6, directs the bicistronic expression of a HA-tagged human TRX (with a modified active site) and of EGFP carrying a farnesylation sequence so as to anchor the marker protein to plasma membranes.

Construction of the Peptide Aptamer Expression Library pBK1, a library of peptide aptamers bearing 10 amino acids within the active site of HA-tagged human TRX was constructed. The oligonucleotides

```
                                                        (SEQ ID 5)
5'-TGGGCCGAGTGGAGCGGTCCG(NNS)9NNCGGACCGAGCAAGATGATCGCCCC-3'
``` where N is A, C, G or T and S is C or G, and

```
5'-GGGGCGATCATCTTGCTCGGTCCG-3'      (SEQ ID 6)
``` were annealed and duplexes were produced using the Klenow DNA polymerase. The AvaII-cut duplexes were ligated into CpoI-cut pVRV6. The ligation product was transformed into ElectroTen Blue competent bacteria (Stratagene) and 8.5× $10^9$ transformants were obtained.

Viral Vector Production

Lentiviral particles were produced by transfecting into 293T cells the following plasmids: i) pVRV6, pVRV12 (pVRV6 directing the expression of p21$^{Cip1}$), pBK1 or any aptamer sub-library; ii) helper pSIV15, directing the expression of gag and pol (20); iii) FbmoSalf, directing the expression of a murine ecotropic envelope (19); iv) pRev (20). In some experiments, plasmids iii and iv were replaced by the G-rev plasmid (20), directing the expression of Rev and the VSV-G pantropic envelope. Lentivirus-containing supernatants were collected and filtered 48 h post-transfection through a 0.45 micron filter. Viral titers were determined by infecting XC or Hela cells and counting GFP-positive cells with a cytometer (FACScan, Becton-Dickinson). From 40% to 100% cells were routinely infected.

Screening of Antiproliferative Peptide Aptamers

XC cells were plated 24 h before infection ($2 \times 10^5$ cells/well, 6-well plates, 6 plates). To infect the cells, a medium containing a viral supernatant and 6 microg/ml polybrene was added. Three days later, the cells were collected, washed with PBS, stained $5 \times 10^5$ cells/ml with 10 microM CellTracker™ Orange CMTMR (Invitrogen) in PBS at 37° C. for 30 min and incubated in culture medium for another 30 min at 37° C. The cells were then plated onto 10 cm dishes ($10^6$ cells/dish). After 72 h, the cells were collected and the highest percentile of CMTMR fluorescent cells was sorted using a FACS Vantage flow cytometer (Becton-Dickinson). The sorted cells were pooled and their genomic DNA was extracted using a Wizard Genomic DNA purification kit (Promega). Aptamer coding genes were PCR amplified using the oligonucleotides

```
5'-AACCGGTGCCTAGAGAAGGT-3'      (SEQ ID 7)

and

5'-AGACCCCTAGGAATGCTCGT-3'.     (SEQ ID 8)
```

The EcoRI/XhoI-digested products were cloned into EcoRI/XhoI-cut pVRV6, to create successive sub-libraries of peptide aptamers, named pCMTMR 1 to 7.

Two-Hybrid Screening of R5G42-Interacting Proteins pVRV6-R5G42 was digested with EcoRI and XhoI and ligated the fragment into EcoRI/XhoI-cut pGILDA (Clontech) to create pGILDA-R5G42, a plasmid directing the galactose-inducible expression of a LexA-R5G42 fusion protein. MB226α pSH18-34 yeast (21) was transformed with pGILDA-R5G42 and MB210a yeast (21) with human foetal brain and human testes cDNA libraries, constructed in pJG4-5. The yeast-two hybrid screening of both libraries was performed essentially as described (21), using $4 \times 10^8$ cfu and $2.4 \times 10^8$ cfu from the brain and testes libraries, respectively. The mating efficiency was estimated at 50% and 58% and the number of diploid exconjugants at $0.2 \times 10^8$ and $1 \times 10^8$ for the brain and testis cDNA library transformed yeast, respectively. The expression of the bait and the libraries were induced at 30° C. for 5 h, from 10% of the diploids. The yeast were collected and plated onto 10 Ura⁻His⁻Trp⁻Leu⁻ galactose/raffinose plates for 5 days, then replica plated onto 10 Ura⁻His⁻Trp⁻Ade⁻ X-gal galactose/raffinose plates. 60 clones were picked from the brain and 48 clones from the testes library that grew in absence of leucine and adenine, and that displayed a β-galactosidase activity. Library plasmids were recovered and re-transformed into EGY48α. The interaction phenotypes were confirmed by a mating assay with EGY42a transformed with pGILDA-R5G42. The library cDNAs were then sequenced from most reconfirmed clones.

Yeast Two-Hybrid Mating Assays

To build the different truncations of the CNAβ Cter interacting clone, oligonucleotides that enabled cloning the PCR products into pJG4-5 by homologous recombination were designed.

```
RH6:                                    (SEQ ID 9)
5'-TTATGATGTGCCAGATTATGCCTCTCCCGAATTCagtatttgctc tgatgatg-3'

RH4:                                    (SEQ ID 10)
5'-AAACCTCTGGCGAAGAAGTCCAAAGCTTCTCGAGCTActgtacag catattccg-3'

RH3:                                    (SEQ ID 11)
5'-AAACCTCTGGCGAAGAAGTCCAAAGCTTCTCGAGCTAggcacttt gcagggtctgc-3'

RH7:                                    (SEQ ID 12)
5'-ACCTCTGGCGAAGAAGTCCAAAGCTTCTCGAGTCAcctgagaaca gagaagact-3'
```

The 5' end of RH6 (upper case) matches part of the HA epitope tag and the 5' ends of RH4, RH3 and RH7 (upper case) match the 5' extremity of the ADH terminator. The PCR reactions was performed using pCMV-SPORT6-CnAβ as a template. CnAβCter Δ1, Δ2, CaM were constructed by combining oligonucleotides RH6/RH4, RH6/RH3, RH6/RH7, respectively. MB210a was co-transformed with the PCR products and EcoRI/XhoI-cut pJG4-5. The prey plasmids were retrieved from the transformants (21) and the homologous recombination products were checked by sequencing. MB210a was also transformed with positive and negative controls of interaction. TB50α was co-transformed with pSH18-34T (a plasmid bearing a high-sensitivity lacZ reporter gene) and pGILDA directing the expression of LexA, LexA-R5G42, LexA-R7G44 and LexA-R5G52. The yeast two-hybrid mating assays were performed as described (21).

In Vitro Binding Assay pVRV6-aptamer plasmids were first digested with EcoRI and XhoI and the fragments were ligated into EcoRI/XhoI-cut pGEX4T1. GST-aptamer fusions were expressed in a BL-21(DE3) *E. coli* strain. Overnight cultures were diluted 1/100 and let to grow at 37° C. to reach an OD$_{600}$ of 0.6 to 0.8. The expression of fusion proteins was induced by adding 1 mM IPTG and incubating overnight at 20° C. with vigorous shaking. The bacteria were collected and resuspended into a lysis buffer (50 mM Tris pH8, 100 mM NaCl, 1 mM DTT) containing 1 mg/ml lysozyme. They were frozen and thawed three times and sonicated on ice. The lysates were centrifuged at 13000 g for 30 min and the soluble fractions were collected. Equal amounts of GST-aptamers were immobilized on 100 μl glutathion sepharose 4B beads (Amersham) at room temperature for 20 min. The beads were washed three times with lysis buffer. The beads were incubated with 1 or 3 μg of bovine brain purified calcineurin (Upstate) for 1 h at 4° C. The beads were then washed five times with lysis buffer and the bound protein was eluted by boiling samples 10 min in presence of electrophoresis loading buffer. The samples were loaded onto a SDS-PAGE, transferred to nitrocellulose membrane, and calcineurin was detected by western-blotting using an anti-calcineurin pan A antibody (1/1000, Chemicon International). The blot was revealed using a HRP-linked rabbit antiserum and an ECL kit (Perkin Elmer).

Cell Proliferation Assay

To stably express peptide aptamers in mammalian cells, the episomal eukaryotic expression vector pCEP4 that bears a CMV promoter and a hygromycin selection marker (InVitrogen) was used. Aptamer coding sequences were PCR amplified using the oligonucleotides

```
5'-GCAAGCTAGCATGTACCCTTATGATGTGCCA-3'   (SEQ ID 13)
``` that hybridized to the HA coding sequence and

```
5'-CGTTGCGGCCGCTTAGACTAATTCATTAATGGT-3'  (SEQ ID 14)
``` that contained a stop codon. The PCR products were digested with NheI and NotI and ligated into NheI/NotI-cut pCEP4 to create pEA-aptamer plasmids. $3 \times 10^5$ cells/well were plated in 6-well plates and transfected 24 h after using Jet PEI (Qbiogen), 3.7 µg pEA-aptamer plasmids and 0.3 µg pEGFP-C1 (Clontech) to monitor transfection. Hygromycin (InVitrogen) was added at 200 µg/ml two days later and the cells were cultured for 2 weeks, renewing the medium twice a week. The cells were then rinsed in PBS and were fixed and stained by incubating 30 min in crystal violet (0.05% crystal violet, 20% ethanol, 0.37% formaldehyde). Excess crystal violet was removed by washing with water.

In Vitro Phosphatase Assay

GST-aptamer fusion proteins were first produced as described above. For this experiment, GST-aptamer fusion proteins were eluted from glutathion sepharose beads using 20 mM reduced L-glutathione (Sigma), and the eluates were dialyzed overnight against a phosphatase buffer (50 mM Tris-HCl pH7.4, 0.1 mM $CaCl_2$). The phosphatase activity of calcineurin was measured using pNPP (Sigma) as substrate, in a final volume of 100 µl. The sample solution contained 50 mM Tris-HCl (pH7.4), 0.1 mM $CaCl_2$, 1 mM $NiSO_4$, 0.15 mg/ml BSA (Sigma), 0.1 µM calcineurin (Upstate). Purified calmodulin (Upstate) and GST-aptamer fusion proteins were added at different concentrations (see figure legend). After a 15 min pre-incubation at 37° C., the reactions were started by adding 4.1 mM pNPP and the mixtures were incubated at 37° C. for 20 min. The nitrophenylate product was measured at 405 nm using an Envision plate reader (Perkin Elmer). The background level that was determined was substracted using a mixture lacking calcineurin.

Monitoring of Bad Phosphorylation

The peptide aptamer coding genes were cloned into pPEAt (a pCEP4-based vector that bears a tetracyclin-inducible promoter and a hygromycin resistance gene), as described above ("cell proliferation assay").

$4 \times 10^5$ Hela-tet cells/well were seeded in a 6-well plate 24 h before transfection. 1 µg of pEBG-mBad (a plasmid directing the expression of the murine Bad protein; Cell Signaling Technology), 0.5 µg of pCMV-SPORT6-CnAβ and pCMV-SPORT6-CnB (plasmids directing the expression of human calcineurin Aβ and B; RZPD), and 1 µg of pPEAt-R5G42, -R5G52 or -R7G44 were transfected with Jet PEI (Qbiogen). After an overnight incubation of the transfection mix, the cells were washed once with culture medium and fresh medium was added, with or without 0.5 µM FK506 (Calbiochem). The cells were collected 24 h later, washed twice in PBS, and lysed 20 min in ice-cold lysis buffer (20 mM Tris, pH 7.4, 150 mM NaCl, 2 mM EDTA, 1% NP40, protease inhibitor cocktail complete EDTA free-Roche). The lysates were centrifuged to remove cellular debris and the protein content was quantified using the microBCA protein assay kit (Pierce). 50 µg of the lysates were loaded on a 4-12% SDS-PAGE, transferred to nitrocellulose membranes, and blotted with anti-phospho-Bad (Ser112), anti-phospho-Bad (Ser136), and anti-Bad antibodies (Cell Signaling Technology). The blots were revealed using the enhanced chemiluminescence (ECL) system (Perkin Elmer).

Raw Cell Differentiation Assay.

Raw1 cells were transfected with the following plasmids: pCI-HA-Trx (negative control), pCI-HA CNA* (positive control for differentiation activation), pCI-HA R5G42, pCI-HA R5G42-C2, pCI-HA R5G42-C7, pCI-HA R5G42-C8 and pCI-HA R5G42-N9. The sequence of CNA* is the same as that of CNA8 (see FIG. 17, SEQ ID 42). The sequences of the R5G42 (SEQ ID 22), C2 (SEQ ID 23), C7 (SEQ ID 27), C8 (SEQ ID 28) and N9 (SEQ ID 33) aptamers is shown on FIG. 8.

One day before the transfection, Raw I cells were plated in 6-well dishes at 50 cell/$mm^2$. Transfection was performed with FuGene 6 Reagent (Roche) using 2 µg of each plasmid and following supplier recommandations.

8 h after transfection D-MEM was changed with α-MEM. In the control dishes α-MEM+50 ng/ml RANKL was added. After 2 days, medium was changed with a fresh medium. The differentiation state was then observed 4 days post-transfection.

Vectors for Yeast Two-Hybrid, Mammalian Cells and In Vivo Assays

The vectors used in the series of experiments are listed in table 3.

The amplification is performed first starting from several isolated bacteria colonies, in 5 ml culture media which allows to obtain a small amount of DNA (Miniprep), sufficient to determine if the cloning was efficient. The genes are then sequenced in order to eliminate errors which could have occurred during the PCR process. If the plasmids are to be used to transfect human or animal cells, a larger quantity is then produced from 300 ml of culture (Maxiprep)

CNA fragments were cloned in HA-pJG4-5 vectors for the yeast two-hybrid analysis preys. The aptamers and mutants of R5G42 were cloned in pCI-HA vectors for the expression in mammalian cells and in pBof (cGFP; double promoter) for expression in animals. pGEX vectors were also prepared for expression of the aptamers in bacteria. The sequences of all vectors were checked.

In Vivo Tibia Muscles Denervation Assay in Mice (Length: 17 Days)

Day 1

General Anaesthesia of the Mice

Four weeks old animals were anaesthetised with a mix of ketamine 50 (PANPHARMA, Ref: PF250211) and Xylazine hydrochloride (Sigma Ref X1251) (⅔, ⅓). Intra-peritoneal injections were performed (120 µl for a 25 g mouse, adjusted in function of the weight).

Injection of the Plasmids in the Ie Tibialis

Mice hind legs were shaved. Both hind legs received an intra-muscular injection with vectors containing TRX, the R5G42, C7 or N9 aptamers, a control aptamer (34) or NaCl (control) in order to obtain an over-expression of a gene in the muscle. The plasmid DNA (purified by cesium chloride) was diluted in NaCl 4.5% filtered 0.22 µm. After disinfection with ethanol 70% of the anterior surface of the tibia, 30 µl containing 5 µg of plasmid DNA containing the aptamer and 2 µg of plasmid DNA containing a nuclear GFP were injected transcutaneously.

Electroporation

An electric field was applied to the muscle to allow the entry of the plasmid DNA into the muscular fibres.

A thin layer of echography gel was applied on both sides of the tibia. The electric field applied corresponded to eight 20 milliseconds impulses spaced by 500 milliseconds, at 200 Volts/cm.

Day 3

Sciatic Denervation

The mouse was positioned on its right flank. The left hind leg and the flank were disinfected. A cutaneous incision was performed in the superior third of the thigh. The conjunctive sheath was cut without harming the two muscular masses beneath. The sciatic nerve can be found between the two masses on passing a forceps in the middle. It was sectioned at two spots at 5 mm from each other, starting from the afferent side. The skin was then sutured.

Day 17

Euthanasia of the Animals

The mice were euthanised by cervical dislocation after general anaesthesia.

The anterior tibialis were removed and fixed on a cork lid with a gum and rapid freezing was performed by diving the whole in liquid nitrogen chilled methycyclohexane. The muscles were thus conserved at −80° C.

Treatment of the Samples

Cryosections

10 μm sections were prepared with a cryostat and placed on slides. The slides were conserved at −80° C.

Immunostaining

The selected slides were treated with the MOM Kit (Vector laboratories, PK-2200).

The sections allow to highlight the slow fibres (MyHC slow antibodies, Sigma, M8421) and the rapid fibres (MyHC Fast, Sigma, M4276).

The developments were performed with DAB (SK-4100) and VIP kits from Vector Laboratories.

The baths were photographed with a binocular magnifier (Binoluminar), at 0.8× optic, and 20× digital enlarging.

The analysis of the surfaces of the muscles was performed with the Metamorph software (version 6).

Tables

TABLE 1

Occurrence of antiproliferative peptide aptamers after the last screening iteration and variable region sequences. Amino acids in lower case correspond to the HTRX flanking residues.

| Peptide Aptamer | Occurrence in $7^{th}$ sub-library | Sequence of variable region |
|---|---|---|
| R5G42 | 0.41 | ... cgpSAVTFAVCALgpc ... |
| R7G11 | 0.09 | ... cgpLHLAGRGWENgpc ... |
| R5G52 | 0.08 | ... cgpIQSPPESPTGgpc ... |
| R7G44 | 0.014 | ... cgpHQSTIGVAEFgpc ... |

TABLE 2

Results of the yeast two-hybrid screening against R5G42. The table lists the different clones selected from the brain and testes libraries and sequenced. Bold numbers correspond to strong, specific two-hybrid interaction phenotypes. Plain numbers correspond to weak, specific interaction phenotypes. Numbers in italics correspond to non-specific clones, which show two-hybrid interaction phenotypes with other peptide aptamers.

| | Brain library | Testes library | Accession Number |
|---|---|---|---|
| CNAβ | | 1 | NP_066955 |
| CNAγ | | 2 | NP_005596 |
| NS5ATP2 | 29 | 9 | NP_057147 |
| Proteasome β 5 subunit | 1 | | NP_002788 |
| Maspardin | 3 | | NP_057714 |
| K channel tetramer. domain | 5 | | NP_076419 |
| Hypothetical protein | | 1 | XP_943453.1 |
| Adaptor protein with PH and SH2 domains | | 1 | NP_066189.1 |
| Sorting nexin 9 | | 1 | NP_057308 |
| CDC42 (GEF9) | | 5 | NP_056000 |
| Promyelocytic leukemia Zn finger protein | | 2 | NP_005997 |
| Fascin 3 | | 1 | NP_065102.1 |

TABLE 3

| | Plasmids | | | | | | | | | | | |
|---|---|---|---|---|---|---|---|---|---|---|---|---|
| | Bacterial Expression | | | Yeast two-hybrid pJG4-5, pGilda, pEG202 | | | | | | Expression mammalian Cells | | |
| Empty plasmids | pGex-4T1 GST Fusion | | | pGilda Bait | | | pJG4-5 Prey | | | pCI-HA HA Tag | | |
| Aptamers | Mini | Maxi | Seq | Mini | Maxi | Seq | Mini | Max | Seq | Mini | Maxi | Seq |
| R5G42 | + | + | + | + | + | + | + | + | + | + | + | + |
| R5G42-C2 | | | | + | + | + | | | | + | + | + |
| R5G42-C7 | + | + | + | + | + | + | | | | + | + | + |
| R5G42-C8 | | | | + | + | + | | | | + | + | + |
| R5G42-N9 | | | | + | + | + | | | | + | + | + |
| R5G52 | + | + | + | + | + | + | | | | + | + | + |
| R5G44 | | | | + | + | + | + | + | + | + | + | + |
| HTrx | + | + | + | + | + | + | | | | + | + | + |

TABLE 3-continued

| | Plasmids | | | | | | | | | | | |
|---|---|---|---|---|---|---|---|---|---|---|---|---|
| | Expression mammalian Cells | | | | | | Expression mouse muscles pBCF | | | Production of recombinant lentivirus | | |
| | pCI-HA pEA Inducible expression | | | pEAt Inducible expression and Tag | | | pBof HA Tag and eGFP co-expression | | | pGREV, pRev, SIV15, pVRV6 pVRV6 | | |
| Empty plasmids Aptamers | Mini | Maxi | Seq | Mini | Maxi | Seq | Mini | Maxi | Seq | Mini | Maxi | Seq |
| R5G42 | + | + | + | + | + | + | + | + | + | + | + | + |
| R5G42-C2 | | | | + | + | + | + | + | + | + | + | + |
| R5G42-C7 | | | | + | + | + | + | + | + | + | + | + |
| R5G42-C8 | | | | | | | + | + | + | + | + | + |
| R5G42-N9 | | | | + | + | + | + | + | + | | | |
| R5G52 | + | + | + | + | + | + | + | + | + | + | + | + |
| R5G44 | + | + | + | + | + | + | + | + | + | + | + | + |
| HTrx | + | + | + | + | + | + | + | + | + | + | + | + |

| | pET15b | | | pEG202 Bait | | | pJG4-5 Prey | | | pCMV | | | pSPORT | | | pCI-HA HA Tag | | |
|---|---|---|---|---|---|---|---|---|---|---|---|---|---|---|---|---|---|---|
| Calcineurin | Mini | Maxi | Seq | Mini | Maxi | Seq | Mini | Max | Seq | Mini | Maxi | Seq | Mini | Maxi | Seq | Mini | Maxi | Seq |
| CNA1 (WT) | | | | + | + | + | + | nn | + | + | + | + | + | + | + | | | |
| CNA2 | | | | | | | + | nn | + | | | | | | | | | |
| CNA3 | | | | | | | + | nn | + | | | | | | | | | |
| CNA4 | | | | | | | + | nn | + | | | | | | | | | |
| CNA5 | | | | | | | + | nn | + | | | | | | | | | |
| CNA6 | | | | | | | + | nn | + | | | | | | | | | |
| CNA7 | | | | | | | + | nn | + | | | | | | | | | |
| CNA8 | | | | | | | + | nn | + | | | | | | | + | + | + |
| CNA9 | | | | | | | + | nn | + | | | | | | | | | |
| CNA10 | | | | | | | + | nn | + | | | | | | | | | |
| CNA11 | | | | | | | + | nn | + | | | | | | | | | |
| CNAγ | + | + | + | | | | + | + | + | | | | | | | | | |

| | pET15b | | | | | | pJG4-5 Prey | | |
|---|---|---|---|---|---|---|---|---|---|
| NS5A-TP2 | Mini | Maxi | Seq | Mini | Maxi | Seq | Mini | Max | Seq |
| NS5A-TP2 | + | + | + | | | | + | + | + |

+: Construction performed in laboratoire
nn: not necessary
mini: Miniprep
maxi: Maxiprep
Seq: Sequencing

REFERENCES

1. Herskowitz, I. (1987) Functional inactivation of genes by dominant negative mutations. Nature 329, 219-222
2. Richardson, J. H. and Marasco, W. A. (1995) Intracellular antibodies: development and therapeutic potential. Trends Biotechnol. 13, 306-310
3. Rimmele, M. (2003) Nucleic acid aptamers as tools and drugs: recent developments. Chembiochem. 4, 963-971
4. Hoppe-Seyler, F., Cmkovic-Mertens, I., Tomai, E. and Butz, K. (2004) Peptide aptamers: specific inhibitors of protein function. Curr. Mol. Med. 4, 529-538
5. Silva, J., Chang, K., Hannon, G. J. and Rivas, F. V. (2004) RNA-interference-based functional genomics in mammalian cells: reverse genetics coming of age. Oncogene 23, 8401-8409
6. Strausberg, R. L. and Schreiber, S. L. (2003) From knowing to controlling: a path from genomics to drugs using small molecule probes. Science 300, 294-295
7. Deiss, L. P. and Kimchi, A. (1991) A genetic tool used to identify thioredoxin as a mediator of a growth inhibitory signal. Science 252, 117-220
8. Gudkov, A. V., Kazarov, A. R., Thimmapaya, R., Axenovich, S. A., Mazo, I. A. and Roninson, I. B. (1994) Cloning mammalian genes by expression selection of genetic suppressor elements: association of kinesin with drug resistance and cell immortalization. Proc. Natl. Acad. Sci. U.S.A. 91, 3744-3748
9. Li, Q. X., Robbins, J. M., Welch, P. J., Wong-Staal, F. and Barber, J. R. (2000) A novel functional genomics approach identifies mTERT as a suppressor of fibroblast transformation. Nucleic Acids Res. 28, 2605-2612
10. Xu, X., Leo, C., Jang, Y., Chan, E., Padilla, D., Huang, B. C., Lin, T., Gururaja, T., Hitoshi, Y., Lorens, J. B. et al. (2001) Dominant effector genetics in mammalian cells. Nat. Genet. 27, 23-29
11. Paddison, P. J., Silva, J. M., Conklin, D. S., Schlabach, M., Li, M., Aruleba, S., Balija, V., O'Shaughnessy, A., Gnoj, L., Scobie, K. et al. (2004) A resource for large-scale RNA-interference-based screens in mammals. Nature 428, 427-431
12. Pestov, D. G. and Lau, L. F. (1994) Genetic selection of growth-inhibitory sequences in mammalian cells. Proc. Natl. Acad. Sci. U.S.A. 91, 12549-12553

13. Hitoshi, Y., Gururaja, T., Pearsall, D. M., Lang, W., Sharma, P., Huang, B., Catalano, S. M., McLaughlin, J., Pali, E., Peelle, B. et al. (2003) Cellular localization and antiproliferative effect of peptides discovered from a functional screen of a retrovirally delivered random peptide library. Chem. Biol. 10, 975-987
14. Colas, P., Cohen, B., Jessen, T., Grishina, I., McCoy, J. and Brent, R. (1996) Genetic selection of peptide aptamers that recognize and inhibit cyclin-dependent kinase 2. Nature 380, 548-550
15. Xu, C. W., Mendelsohn, A. R. and Brent, R. (1997) Cells that register logical relationships among proteins. Proc. Natl. Acad. Sci. U.S.A. 94, 12473-12478
16. Geyer, C. R., Colman-Lerner, A. and Brent, R. (1999) "Mutagenesis" by peptide aptamers identifies genetic network members and pathway connections. Proc. Natl. Acad. Sci. U.S.A. 96, 8567-8572
17. Norman, T. C., Smith, D. L., Sorger, P. K., Drees, B. L., O'Rourke, S. M., Hughes, T. R., Roberts, C. J., Friend, S. H., Fields, S. and Murray, A. W. (1999) Genetic selection of peptide inhibitors of biological pathways. Science 285, 591-595
18. Blum, J. H., Dove, S. L., Hochschild, A. and Mekalanos, J. J. (2000) Isolation of peptide aptamers that inhibit intracellular processes. Proc. Natl. Acad. Sci. U.S.A. 97, 2241-2246
19. Mangeot, P. E., Duperrier, K., Negre, D., Boson, B., Rigal, D., Cosset, F. L. and Darlix, J. L. (2002) High levels of transduction of human dendritic cells with optimized SIV vectors. Mol. Ther. 5, 283-290
20. Negre, D., Mangeot, P. E., Duisit, G., Blanchard, S., Vidalain, P. O., Leissner, P., Winter, A. J., Rabourdin-Combe, C., Mehtali, M., Moullier, P. et al. (2000) Characterization of novel safe lentiviral vectors derived from simian immunodeficiency virus (SIVmac251) that efficiently transduce mature human dendritic cells. Gene Ther. 7, 1613-1623
21. Bickle, M., Dusserre, E., Moncorgé, O., Boffin, H. and Colas, P. (2006) Selection and characterization of large collections of peptide aptamers through optimized yeast two-hybrid procedures. Nat. Protoc. in press
22. Yang, Q., Cheng, J., Liu, Y., Hong, Y., Wang, J. J. and Zhang, S. L. (2004) Cloning and identification of NS5ATP2 gene and its spliced variant transactivated by hepatitis C virus non-structural protein 5A. World J. Gastroenterol. 10, 1735-1739
23. Aramburu, J., Heitman, J. and Crabtree, G. R. (2004) Calcineurin: a central controller of signalling in eukaryotes. EMBO Rep. 5, 343-348
24. Kahl, C. R. and Means, A. R. (2003) Regulation of cell cycle progression by calcium/calmodulin-dependent pathways. Endocr. Rev. 24, 719-736
25. Wang, H. G., Pathan, N., Ethell, I. M., Krajewski, S., Yamaguchi, Y., Shibasaki, F., McKeon, F., Bobo, T., Franke, T. F. and Reed, J. C. (1999) Ca2+-induced apoptosis through calcineurin dephosphorylation of BAD. Science 284, 339-343
26. Ke, H. and Huai, Q. (2003) Structures of calcineurin and its complexes with immunophilins-immunosuppressants. Biochem. Biophys. Res. Commun. 311, 1095-1102
27. Baines, I. C. and Colas, P. (2006) Peptide aptamers as guides for small molecule drug discovery. Drug Disc. Today, 11, 334-341
28. Gururaja, T., Li, W., Catalano, S., Bogenberger, J., Zheng, J., Keller, B., Vialard, J., Janicot, M., Li, L., Hitoshi, Y. et al. (2003) Cellular interacting proteins of functional screen-derived antiproliferative and cytotoxic peptides discovered using shotgun peptide sequencing. Chem. Biol. 10, 927-937
29. Hogan P. G., Chen L., Nardone J. and Rao A. (2003) Transcriptional regulation by calcium,calcineurin, and NFAT. Genes and Dev. 17, 2205-2232
30. Asagiri M, Takayanagi H. The molecular understanding of osteoclast differentiation. Bone 40 (2006) 251-264
31. Zhu L L, et al. RANK-L induced the expression of NFATc1, but not of NFkB subunits durino osteoclast formation. Biochemical and Biophysical Research Communications 326(2005) 131-135
32. Takayanagi H et al, Induction and activation of the transcription factor NFATc1 integrate RANKL signaling for terminal differentiation of osteoclasts. Dev Cell 3 (2002) 889-901

---

The invention claimed is:

1. An isolated polypeptide comprising or consisting essentially of:
   (i) the amino acid sequence SAVTFAVCAL (SEQ ID 20), or
   (ii) the amino acid sequence GPSAVTFAVCALGP (SEQ ID 21), or
   (iii) a variant of the amino acid sequence (i) or (ii) having one amino acid changed,
   wherein said polypeptide is capable of binding to:
   (a) a protein which comprises at least the sequence extending from amino acid 378 to 500 of the beta isoform of calcineurin A (SEQ ID NO:17),
   (b) the alpha isoform of calcineurin A (SEQ ID NO:16),
   (c) the beta isoform of calcineurin A (SEQ ID NO:17),
   (d) the gamma form of calcineurin A (SEQ ID NO:18) or
   (e) NS5A-TP2 (SEQ ID NO:15).

2. A polypeptide according to claim 1, having a modulatory effect on a cell, wherein said cell is a eukaryotic cell, a mammalian cell, an animal cell, a murine cell or a human cell.

3. A polypeptide according to claim 2, wherein said cell is a muscle, bone, neuronal or cardiac cell.

4. A polypeptide according to claim 2, wherein said polypeptide has an antiproliferative or differentiating effect on said cell.

5. A polypeptide according to claim 2, wherein said polypeptide activates NFAT.

6. A polypeptide according to claim 1, wherein said amino acid sequence (i), (ii) or (iii) is conformationally constrained by covalently binding to a scaffold molecule.

7. A polypeptide according to claim 6, wherein said amino acid sequence (i), (ii) or (iii) is bound to the scaffold at both C and N termini.

8. A polypeptide according to claim 7, wherein said amino acid sequence (i), (ii) or (iii) is located between two cysteines.

9. A polypeptide according to claim 6, wherein the scaffold molecule is a thioredoxin, a thioredoxin-like protein, a nuclease, a protease, a protease inhibitor, an antibody or a structurally-rigid fragment of an antibody, a fluorescent protein, or a conotoxin.

10. A polypeptide according to claim 9, wherein the scaffold molecule is human thioredoxin and said amino acid sequence i), (ii) or (iii) is located between the two cysteines located at positions 32 and 35.

11. A polypeptide according to claim 1, which binds to calcineurin through said amino acid sequence (i), (ii) or (iii).

12. A polypeptide according to claim 1, which binds to the calcineurin A subunit.

13. A polypeptide according to claim 12, which binds to at least one of the alpha, beta, or gamma isoforms of human calcineurin A (CNA).

14. A polypeptide according to claim 12 which binds to CNA at a site located within the sequence extending from the amino terminal of the calmodulin binding domain to the carboxy terminal of the auto-inhibitory domain of CNA, wherein said site is not limited to the calmodulin binding domain.

15. A polypeptide according to claim 13 which binds to the human CNA beta isoform at a site located within the sequence extending from amino acid 378 to 500.

16. A fusion protein comprising the polypeptide of claim 1 covalently bound at its amino or carboxy terminus to another protein.

17. A polypeptide according to claim 1, wherein said polypeptide has an differentiating effect on osteoclasts in the absence of RANKL.

18. A polypeptide according to claim 9, wherein the scaffold molecule is RNaseA, trypsin, eglin C, GFP, YFP, human thioredoxin, or *E. coli* thioredoxin A.

* * * * *